United States Patent [19]
Elings et al.

[11] Patent Number: 5,866,807
[45] Date of Patent: Feb. 2, 1999

[54] METHOD AND APPARATUS FOR MEASURING MECHANICAL PROPERTIES ON A SMALL SCALE

[75] Inventors: Jeffrey R. Elings; Virgil B. Elings; Christopher C. Schmitt, all of Santa Barbara, Calif.

[73] Assignee: Digital Instruments, Santa Barbara, Calif.

[21] Appl. No.: 794,379

[22] Filed: Feb. 4, 1997

[51] Int. Cl.⁶ .............................. G01B 11/30; G01N 3/46
[52] U.S. Cl. ................................................. 73/105; 73/81
[58] Field of Search ..................... 73/155, 81; 250/306, 250/307

[56] References Cited

U.S. PATENT DOCUMENTS

| | | | |
|---|---|---|---|
| Re. 33,387 | 10/1990 | Binnig ..................................... | 250/306 |
| Re. 34,331 | 8/1993 | Elings et al. ............................. | 250/306 |
| Re. 34,489 | 12/1993 | Hansma et al. ......................... | 250/560 |
| 4,848,141 | 7/1989 | Oliver et al. ............................. | 73/81 |
| 5,193,383 | 3/1993 | Burnham et al. ........................ | 73/105 |
| 5,229,606 | 7/1993 | Elings et al. ............................. | 250/306 |
| 5,266,801 | 11/1993 | Elings et al. ............................. | 250/306 |
| 5,329,808 | 7/1994 | Elings et al. ............................. | 73/105 |
| 5,383,354 | 1/1995 | Doris et al. ............................... | 73/105 |
| 5,400,647 | 3/1995 | Elings ...................................... | 73/105 |
| 5,406,832 | 4/1995 | Gamble et al. .......................... | 73/105 |
| 5,412,980 | 5/1995 | Elings et al. ............................. | 73/105 |
| 5,415,027 | 5/1995 | Elings et al. ............................. | 73/105 |
| 5,461,907 | 10/1995 | Tench et al. ............................. | 73/105 |
| 5,463,897 | 11/1995 | Prater et al. ............................. | 73/105 |
| 5,481,908 | 1/1996 | Gamble .................................... | 73/105 |
| 5,497,656 | 3/1996 | Kado et al. ............................... | 73/105 |
| 5,504,338 | 4/1996 | Marrian et al. ..................... | 250/306 X |
| 5,519,212 | 5/1996 | Elings et al. ........................ | 73/105 X |
| 5,553,486 | 9/1996 | Bonin ....................................... | 73/105 |
| 5,557,156 | 9/1996 | Elings ...................................... | 310/316 |
| 5,574,278 | 11/1996 | Poirier ..................................... | 250/306 |

OTHER PUBLICATIONS

Friction Effects on Force Measurements with an Atomic Force Microscope, Jan H. Hoh and Andreas Engel, Aug. 3, 1993. 3 pages.

Nanoindentation Hardness Measurements Using Atomic Force Microscopy, Bharat Bhushan and Vilas N. Koinkar, Applied Phys. Lett. 64 (13), Mar. 28, 1994. pp. 1653–1655.

In situ Imaging of $\mu$N Load Indents into GaAs, E.T. Lilleodden, W. Bonin, J. Nelson,J.T. Wyrobek, W.W. Gerberich, J. Mater. Res., vol. 10, No. 9, Sep. 1995. pp. 2162–2165.

An Improved Technique for Determining Hardness and Elastic Modulus Using Load and Displacement Sensing Indentation Experiments, W.C. Oliver & G.M. Pharr, J. Mater. Res., vol. 7, No.6, Jun 1992. pp. 1564–1583.

TappingMode™ Imaging Applications and Technology, C.B. Prater, P.G. Maivald, K.J. Kjoller and M.G. Heaton; Digital Instruments 7 pages by Apr. 1997.

Nanoindentation and Hardness Testing with NanoScope® SMPs, J.R. Elings, Digital Instruments, Jan. 1996 4 pages.

Tip Surface Interactions in STM and AFM, J.B. Pethica and W.C. Oliver, Physica Scripta, vol. T19, 61–66, 1987. Month not given.

Atomic Force Microscope, G. Binnig and C.F. Quate, Physical Review Letters, vol. 56, No. 9., Mar. 3, 1986. pp. 930–933.

(List continued on next page.)

Primary Examiner—Thomas P. Noland
Attorney, Agent, or Firm—Nilles & Nilles, S.C.

[57] ABSTRACT

The mechanical properties of a surface are measured by using a pointed tip on the end of a bendable cantilever such that with force on the other end of the cantilever the tip can be pushed into the surface using the bending of the cantilever as the measure of the constant force. The indentation, scratch, or wear created by the application of forces between the tip and sample is then measured with the same tip and cantilever by raising the cantilever off the surface and putting it into oscillation. The tip is then scanned over the area where the indentation was made with the tip tapping on the surface in order to image the surface.

9 Claims, 17 Drawing Sheets

OTHER PUBLICATIONS

*Scanning Tunneling Microscopy and Atomic Force Microscopy: Application to Biology and Technology*, P.K. Hansma, V.B. Elings, O. Marti, C.E. Bracker, Science, vol. 242, pp. 209–216, Oct. 14, 1988.

*Energy Dissipation During Nanoscale Indentation of Polymers with an Atomic Force Microscope*, E. Boschung, M. Heuberger, and G. Dietler, Appl. Phys. Lett. 64 (14), Apr. 1994. pp. 1794–1796.

*Nanotribology: Friction, Wear and Lubrication at the Atomic Scale*, B. Bhushan, J. Israelachvili and U. Landman, Nature, vol. 374, pp. 607–616, Apr. 1995.

*Micromachining with a Force Microscope Tip Assisted by Electrostatic Force*, K. Goto and K. Hane, Rev. Sci. Instrium. 67 (2), Feb. 1996, pp. 397–400.

*Imaging Metal Atoms in Air and Water Using the Atomic Force Microscope*, S. Manne, H.J. Butt, A.C. Gould, and P.K. Hansma, Appl. Phys. Lett. 56 (18), Apr. 1990, pp. 1758–1759.

*Atomic Force Microscopy*, Daniel Rugar and Paul Hansma, Physics Today, Oct. 1990, pp. 23–30.

*Nanoindentation Hardness Tests Using a Point Contact Microscope*, C.J. Lu, D.Bogy and R. Kaneko, Journal of Tribology, vol. 116, Jan. 1994, pp. 175–180.

METHOD AND APPARATUS FOR MEASURING MECHANICAL PROPERTIES ON A SMALL SCALE

BACKGROUND OF THE INVENTION

1. Field of Invention

This invention relates generally to methods and systems for measuring mechanical properties of materials, and more specifically to improvements in microindentation methods for measuring mechanical properties of materials.

2. Discussion of the Background

An Atomic Force Microscope ("AFM"), as described in U.S. Pat. No. RE 34,489, by Hansma et al., is a type of scanning probe microscope ("SPM"). AFM's are high resolution surface measuring instruments. Two general types of AFMs are relevant here, the contact mode (repulsive mode), and the intermittent contact mode AFM.

The contact mode AFM is described in detail in U.S. Pat. No. RE34,489 by Hansma et al. This AFM operates by placing a sharp tip attached to a bendable cantilever directly on a surface and then scanning the surface laterally. The bending of the lever in response to surface height variations is monitored by a detection system. Typically, the height of the fixed end of the cantilever relative to the sample is adjusted with feedback to maintain the bending at a predetermined amount during lateral scanning. The adjustment amount versus lateral position creates a map of the surface. The deflection detection system is typically an optical beam system as described by Hansma et al. Using very small microfabricated cantilevers and piezoelectric positioners as lateral and vertical scanners, AFMs can have resolution down to the molecular level, and may operate with controllable forces small enough to image biological substances.

The intermittent contact mode AFM utilizes oscillation of a cantilever to, among other things, reduce the forces exerted on a sample during scanning. This type of AFM is described in U.S. Pat. Nos. 5,226,801, and 5,415,027 by Elings et al. In U.S. Pat. No. 5,412,980 by Elings et al, an atomic force microscope is disclosed in which a probe tip on a cantilever is oscillated at or near a resonant frequency and at a predetermined amplitude called the setpoint and is scanned across the surface of a sample in intermittent contact with the sample. The setpoint is the value of the amplitude of oscillation of the cantilever which is desired while imaging the sample in intermittent contact mode. The amplitude of the cantilever is kept constant by feedback at a value equal to the setpoint. (Similarly, for contact mode, the setpoint is the value of the deflection of the cantilever which is desired while imaging the sample and is kept constant by feedback.) The amplitude of oscillation of the probe is kept constant through feedback which servos the vertical position of the cantilever mount or sample so that the probe follows the topography of the sample surface. The probe's oscillation amplitude is usually greater than 20 nm to maintain the energy in the lever arm much higher than the energy it loses in each cycle by striking the sample surface. This prevents the probe tip from sticking to the sample surface. Sample height data is obtained from the Z actuator control signal produced to maintain the established setpoint.

3. Description of the Related Art

The problem is to perform very small indentations into only the surface of a sample to measure just that surface's mechanical properties, such as hardness and elasticity. For instance, a substance such as diamond-like carbon may be deposited as a 10 nm thick film to give a hard surface to objects such as magnetic disks for data recording. It would be useful to be able to measure the hardness, wearability, adhesion, thickness and topography of these deposited films without inadvertently measuring the hardness of the substrate on which the film is deposited. Thus, accuracy in the depth of the indentation is critical to avoid penetration of the substrate by the tip or to wear and scratch only the film during a measurement.

The related art can provide accuracy by pairing a force/displacement transducer that uses columnar compression to produce force, rather than bending of a cantilever, with an STM or an AFM, as described in U.S. Pat. No. 4,848,141 by Oliver et al. Having made such a small indentation, it is both difficult to find the indentation on the surface in order to measure it, and difficult to measure if it can be found. See: Lilleodden et al., "In Situ Imaging of $\mu$N Load Indents into GaAs", *J. Mater. Res.*, Vol. 10, No. 9, 9/1995, and Bhushan et al., "Nanoindentation hardness measurements using atomic force microscopy", *Appl. Phys. Lett.* 64 (13), 28 Mar. 1994. The dents made by nanoindentation are usually so small that they cannot be imaged except by AFMs. Prior methods of indentation using non-AFM indenters require that the sample be moved from the indenter to an AFM to image the dent. To deal with these problems, both Lilleodden et al. and Bhushan et al. used the same tip for indentation and imaging. It is advantageous to use the same tip because the indent area remains in a known position rather than being lost while the tips are changed (Lilleodden et al.).

However, the related art encountered the further problem that using the same force detection transducer for both indentation and scanning is difficult because the optimal forces for each are orders of magnitude apart. For indentation, one may need 1000 times the force as is necessary for a non-destructive scan over the surface. According to the related art, to be able to use the same tip for both indenting and measurement, one must compromise by having either an artificially low indentation force, or a stiff cantilever that applies a high scanning force that is destructive to the sample.

Thus, it would be advantageous to have a method where the same tip could be used to apply large indentation forces to hard surfaces, and to apply very small forces for imaging the surface of the sample with high sensitivity.

As will be described, the current invention achieves high sensitivity through oscillation of the probe tip. As discussed above, Elings et al. discuss an intermittent contact, "tapping," AFM in U.S. Pat. Nos. 5,412,980 and 5,415,027 that provides sufficient sensitivity, but this has not previously been used in conjunction with indenting. Nano Instruments provides an indenter that oscillates its indenting tip while indenting. As used by Oliver et al., however, the tip is not used to image the sample, is not mounted on a cantilever, and is not necessarily oscillated at its resonant frequency. Oliver et al., "An Improved Technique for Determining Hardness and Elastic Modulus using Load and Displacement Sensing Indentation Experiments," *J. Mater. Res.*, Vol. 7, No. 6, June 1992. Thus, the oscillation of the indenter is not used to reduce the force exerted on the sample during imaging.

There is also significant interest in determining the toughness, film adhesion, wearability and durability of thin films on a very small scale. Scratching and wear testing can yield data on film adhesion values, toughness/durability of films, and thickness of the films. However, for the same reasons that it is difficult to use the same stiff cantilever to make a dent and to then image the dent, it is also difficult to use the same tip to scratch or wear hard samples and then apply a small force to image the sample just scratched or worn. The scratches, like dents, are usually so small that they cannot be imaged except with an AFM. Thus, the advantages of indenting discussed herein apply equally to both scratching and wear testing. It is preferable to make an image of the scratch or wear test to examine the nature of the scratch or wear. For instance, when testing a thin film, it may be advantageous to see if the film lifts off the surface, i.e., to check its adhesion or to measure the thickness of the lifted edge.

SUMMARY OF THE INVENTION

Wherefore, an object of this invention is to provide an instrument that can both indent and measure a sample on a very small scale and with high sensitivity.

It is another object of this invention to provide a microscope wherein a large range of forces may be exerted between a sample and a single probe tip.

It is another object of this invention to provide a microscope wherein large indentation forces may be applied in order to indent hard surfaces, but also allowing for very small forces to be utilized for imaging a surface without changing probe tips.

It is another object of this invention to measure the force exerted by the tip at discrete points in time and continually during indenting.

It is another object of this invention to provide a microscope wherein the same probe tip may be used for both scratching and measuring the surface of a sample on a very small scale.

It is another object of this invention to provide a microscope wherein the same probe tip may be used for both wearing and measuring the surface of a sample on a very small scale.

Other objects and benefits of the invention will become apparent from the description which follows hereinafter when taken in conjunction with the drawing figures which accompany it.

According to the present invention, the mechanical properties of a surface are measured by using a pointed tip on the end of a bendable cantilever such that, when a force is imposed on the fixed end of the cantilever, the tip is pushed against the surface using the deflection of the cantilever as the measure of the force. Any extraneous forces between the tip and sample caused by bend or flex of the cantilever may be corrected for by relative X and Y plane motion between the tip and sample. The indentation is then measured with the same tip and cantilever by raising the tip off the surface and putting the cantilever into oscillation. The tip is then scanned over the area where the indentation was made with the tip tapping on the surface according to operation in intermittent contact mode.

It is an advantage of the invention that the force required to indent a sample may be produced with a stiff cantilever, and the sensitivity required for imaging with the same cantilever is provided by the tapping function of the instrument.

It is another advantage of the invention that the force required to scratch a sample may be produced with a cantilever and the tip sensitivity required for imaging the scratch is still available because of the tapping function of the instrument.

It is another advantage of the invention that the force required to wear a sample may be produced with a stiff cantilever and the sensitivity required for imaging with the same cantilever is provided by the tapping function of the instrument.

It is desirable to measure the elasticity of a sample on a very small (micro) scale because its elasticity on that micro scale may differ greatly from its macro elasticity. The micro elasticity of a sample may be determined using the present invention by a comparison of the depth of a dent to the area of the dent at the sample's surface plane. Maximum tip penetration depth may also be derived from measuring the area of the dent soon after the dent is made.

It is another advantage of the invention that without changing tips the local elasticity of a sample may be determined by a comparison of the dent's depth to its area. When the tip is retracted from the surface after indentation, the material that was deformed by the tip may recover elastically making the indentation more shallow than the actual tip shape that made the indentation. By imaging the indentation and measuring its shape, one can get a relative measure of the elasticity of the surface.

It is another advantage of this invention that, prior to indenting, the probe can be brought down very near to the surface by sensing the surface using the oscillation of the cantilever. This is an advantage because the deflection signal of the cantilever can change slightly as the probe approaches the surface. Thus, the deflection at a vertical position very close to the sample can give a better indication of when zero force is being applied to the sample. The deflection of the cantilever can then be measured relative to this zero force value for deflection. Thus, the deflection of the cantilever due to contact with the surface can be more accurately known which allows more accurate force to be applied.

It is another advantage that the surface can be imaged without damage before indentation, in order to position the indentation or scratch at a particular place on the sample.

It is another advantage of the invention that extraneous lateral forces otherwise exerted by the tip during indenting are corrected by relative motion between the tip and sample in the X and Y directions of the scan.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIGS. 13a–13e illustrate the effects on a sample surface of indenting with and without X-Y compensation.

DETAILED DESCRIPTION OF THE PREFERRED EMBODIMENTS

The present invention utilizes the inventors' discovery that a probe with a stiff cantilever may be used to indent a sample and the same probe may be oscillated at or near its resonant frequency and tapped on a sample so that it may be used to image the sample and the dent it just made. This desirable combination is possible because stiff cantilevers will provide the necessary force to indent a sample while intermittent contact mode can still apply very small forces for imaging the sample with the same cantilevers.

According to the present invention, the AFM is operated in both indenting and intermittent contact modes. FIGS. 2 through 11 represent the preferred embodiments of the invention. Three phases are described for each of three preferred embodiments because the invention is most easily understood as three different functions of a single instrument that are performed together and are dependent on each other. The first phase, where the tip approaches the surface of the sample, may be accomplished in other ways than it is presented here, but the preferred embodiment includes a method for that phase for clarity of understanding. The type of approach presented is therefore not a necessary part of the present invention.

The first preferred embodiment of the present invention is indenting, where a dent is made in the sample surface. The second is scratching, where indenting is coupled with horizontal movement to form a scratch in the sample surface. The third is wearing, where a number of scratches are made in a given area on the sample surface.

For all three of these preferred embodiments, the first phase is an approach procedure that finds the surface of the sample. The second phase is application of force between the cantilever and the sample to press the tip into the sample and create a dent or scratch. The third phase is imaging and measurement of the area of the sample that includes the new topographic features.

Figure 1:
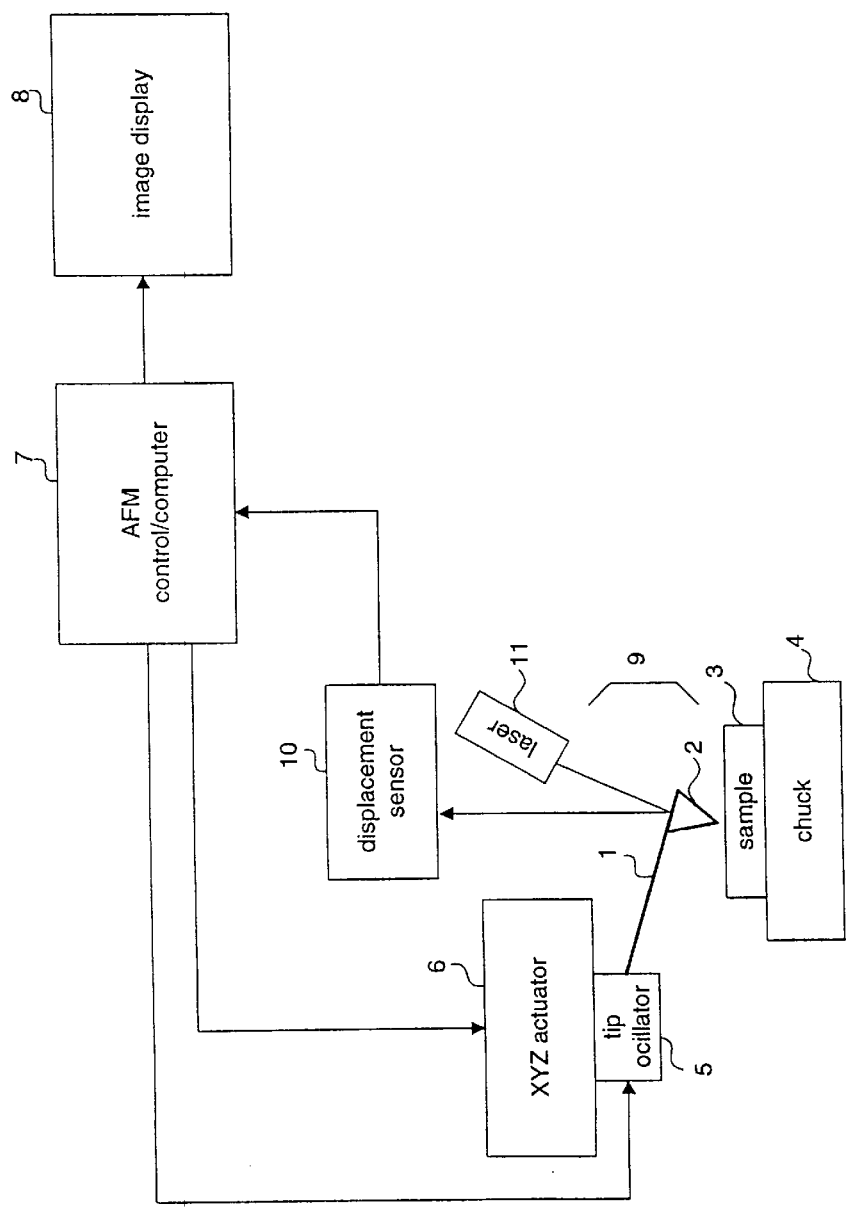
FIG. 1 is a simplified functional block diagram of an atomic force microscope incorporating the present invention.

Referring to FIG. 1, the probe 9 of an AFM microscope constructed in accordance with a preferred embodiment of the invention includes a tip 2 mounted on a cantilever 1. The tip 2 is a very small three-sided (not including base) pyramid shaped diamond mounted at the free end of the cantilever 1 and having an apex. The diamond tip radius is typically less than 50 nm, and the diamond side length is typically between 10 and 150 microns. The cantilever 1, preferably formed from stainless steel foil, is typically between 300 and 800 microns long, most typically 400 microns long, 100 microns wide and 13 microns thick, with a typical spring constant of between 100 Newtons/meter (N/m) and 400 N/m, most typically about 150 N/m, and a resonant frequency of about 40 kHz. It is important to use a small diamond to keep the mass very small so that the resonant frequency can be as high as possible. The inventors have made diamond tips as short as 20 microns. Ordinarily, the diamond tip 2 is glued to the free end of the cantilever 1 while the fixed end of the cantilever 1 is mounted in a holder. The diamond can be cut so that its long axis is at an angle equal to the cantilever tilt with respect to the sample so that the diamond makes a symmetric dent.

The cantilever 1 is also in contact with a tip oscillator 5 that may, for example, comprise a piezo bi-morph stack that is placed such that when an AC voltage is applied to the oscillator 5, the cantilever 1 is oscillated at a controllable frequency. The cantilever 1 could also be oscillated with an electric field acting directly on the cantilever. The cantilever could be made of magnetic material such as nickel and oscillated with an oscillating magnetic field.

To detect bending of the cantilever 1, a laser 11 is typically used to generate a signal that is reflected off the back of the free end of the cantilever 1 onto displacement sensor 10 which registers the cantilever's bending as the reflected spot moves across it. Other methods of detecting the bending include using an optical interferometer or a strain gauge on the cantilever. The tip holder is usually mounted at the end of a piezoelectric tube. The tube is bent by application of voltages to its sides, producing relative motion between the tip and a sample disposed beneath it. Rather than moving the tip over the sample, other embodiments move the sample beneath the tip.

The dimensions and stiffness of the cantilever 1 are to be distinguished from the dimensions and stiffness of a cantilever of a probe which is configured for imaging without indenting and which has a standard silicon tip. The standard non-indenting tapping cantilever has a length of only about 100 to 250 microns, and a spring constant of typically 20 to 100 N/m or less assuming that the cantilever has a thickness of between 3 to 6 microns. Hence, the cantilever 1 is considerably longer and thicker and much stiffer than standard imaging cantilevers and has a much harder tip. Its 40 kHz resonant frequency is also substantially less than the 200 to 400 kHz resonant frequency of standard silicon probes but still high enough to image in tapping mode at acceptable speeds. A standard silicon nitride contact cantilever is again 100 to 200 microns long, but with a force constant of about 0.5 N/m so that the tip will not be damaged when it is in constant contact with the sample.

Thus, in a typical arrangement, the tip 2 may be scanned across the sample 3 to a particular point by the piezo tube, force is then applied between the tip and sample, also by the piezo tube, to create a dent in the sample, and the tip is then oscillated by the piezo bi-morph stack so that it is just tapping the surface to image the area of the sample including the dent. This description hereby incorporates by reference U.S. Pat. Nos. 5,463,897 by Prater et al. and 5,412,980 by Elings et al., which describe this structure and operation without the indenting function.

1. Indenting

Figure 12A:
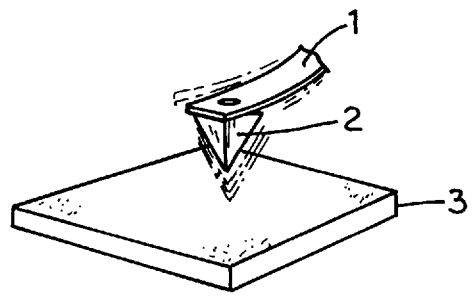
FIG. 12a–12e are simplified perspective views illustrating an indenting operation using an atomic force microscope constructed in accordance with the present invention.
Figure 12B:
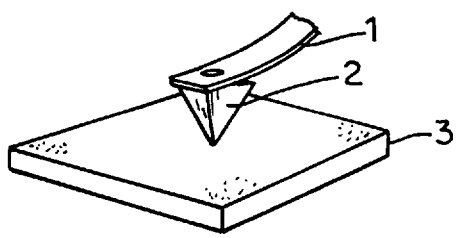
Figure 12C:
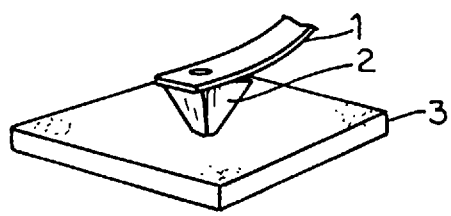
Figure 12D:
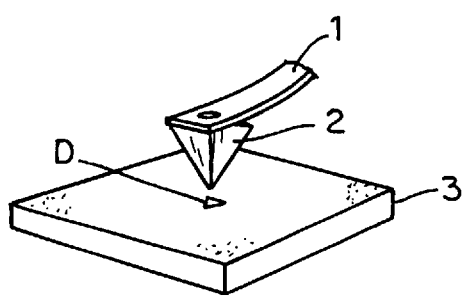
Figure 12E:
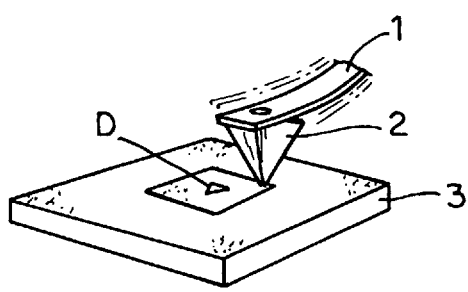

In the preferred embodiment, a sample 3 is placed on an X-Y translator, preferably a chuck 4, and the AFM probe 9 is brought down, while oscillating, into intermittent contact with the sample as seen in FIG. 12a such that the amplitude of the oscillations of the probe 9 is reduced to a predetermined amplitude. Tip and sample interaction other than intermittent contact can be detected and used in a similar manner, but the preferred embodiment utilizes intermittent contact. This process is used to locate the surface, and to move the tip 2 close to the sample prior to indenting. As stated above, this approach procedure could be accomplished in a number of ways without changing the claimed present invention. The probe tip 2 is then pushed into the sample as illustrated by FIGS. 12b and 12c until, in the preferred embodiment, a predetermined deflection of by the cantilever (force) is reached. Both the cantilever deflection and the vertical position are recorded. During this phase, the tip oscillator 5 is ordinarily turned off. Alternatively, if it is not turned off, the inventors have found that the oscillation of the tip 2 effectively ceases when the tip 2 is pushed against the surface of the sample 3. Typically, both oscillation amplitude and cantilever deflection (during approach and imaging) are measured with the displacement sensor 10 as described in Hansma, U.S. Pat. No. RE34,489, Prater et al., U.S. Pat. No. 5,463,897 and Elings et al., U.S. Pat. No. 5,412,980, but could also be measured by an optical interferometer or a strain gauge on the cantilever. At the predetermined deflection, the probe is lifted away from the surface back to its initial position. This force application can be performed either with a predetermined indentation (as related to a desired force) or with a feedback function to control depth, force or other variables. After making the dent D (FIGS. 12d and 12e), the probe 9 is then retracted from contact with the sample 3 by actuation of the XYZ actuator 6. This procedure may be repeated to create as many dents at as many forces and locations as desired. To image the dent or dents D just made, the retracted probe 9 is again set into intermittent contact mode oscillation as illustrated in FIG. 12e and the area on the sample 3 including the dent is then imaged with the same probe in intermittent contact mode according generally to U.S. Pat. No. 5,412,980 by Elings et al.

In order to reduce instrumental drifts, it may be advantageous to do the indentation very quickly. To accomplish this, the tip 2 should be very close to the surface (usually within 2 to 50 nm, with a preferred range of 6 to 10 nm) so that it can be brought down quickly and made to indent the surface. A single indenting usually takes between 0.5 and 1 second, but may be done as rapidly as 0.01 seconds and as slowly as 100 seconds. This range may be even wider if the user desires to measure slow moving sample or scanner characteristics such as creep. The tip 2 is then pulled up quickly to prevent instrumental drift from dragging the tip across the surface during indentation. Where instrumental drift does not exist or is compensated for, the speed of the indent becomes less important.

Figure 10A:
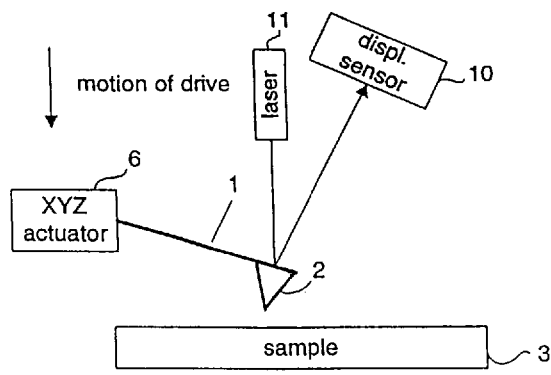
FIGS. 10a–10d are a set of diagrams depicting indenting with and without X-Y compensation.
Figure 10B:
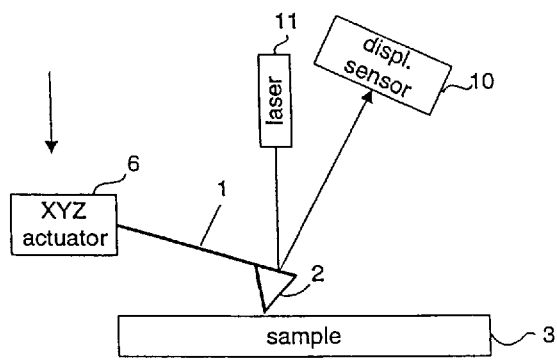
Figure 10C:
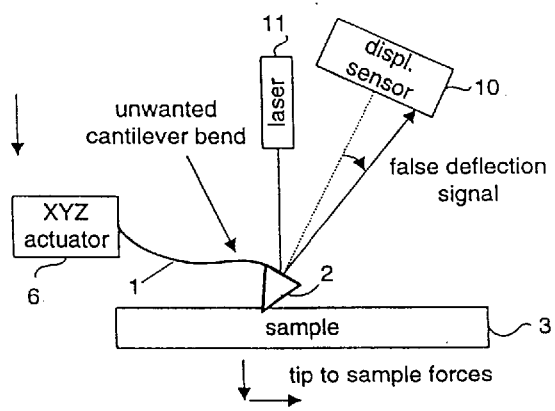
Figure 10D:
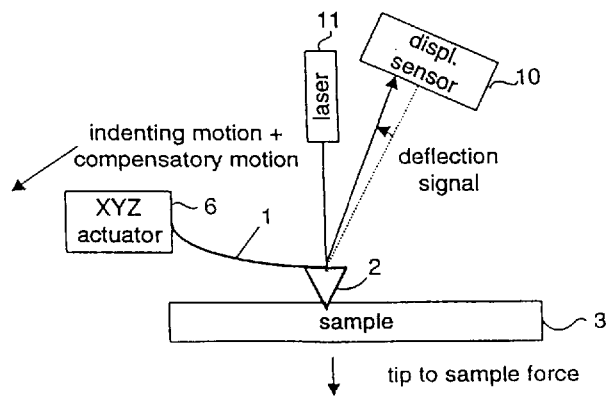

It is an advantage of the invention that extraneous forces between the tip 2 and sample 3 caused by the indenting are compensated for ("X-Y compensation") to prevent unwanted lateral forces during indenting. Because the tip 2 penetrates the surface of the sample 3 and is held at that point by sticking into the surface, the continued downward motion of the cantilever 1, can flex or twist the cantilever 1 with respect to the sample as illustrated in FIG. 10c and thereby cause erroneous deflection signals. That flex or twist then creates unwanted extraneous forces between the tip 2 and sample 3 that can interfere with the indent. The flex or twist causes the beam produced by laser 11 to move on the displacement sensor 10 in a direction opposite to the direction caused by deflection of the cantilever 1 giving a false deflection signal (see FIG. 10C). This causes the feedback to move the probe 9 down, using the XYZ actuator 6, in order to compensate for the false deflection signal. Thus, a force is applied to the sample that is larger than the force calculated from the deflection as seen by the displacement sensor 10. (See FIGS. 10A–10D). This unwanted cantilever bending is compensated for by relative horizontal motion between the cantilever 1 and sample 3 as illustrated in FIG. 10d. This relative horizontal motion maintains the drive motion of the cantilever 1 substantially perpendicular to the longitudinal axis of the cantilever 1 so that the force exerted between the tip 2 and the sample 3 is normal to the cantilever 1.

If the long axis of the cantilever 1 is parallel to the sample 3, the free end of the cantilever 1 may be moved perpendicular to the sample plane without causing extraneous lateral forces due to lateral motion. However, in most AFMs the cantilever 1 is at an angle with respect to the sample, as shown in FIGS. 10a–10d. The cantilever or sample therefore must be moved at some angle to keep the motion of the cantilever 1 perpendicular to the long axis of the cantilever 1. One way that the inventors have done this is to control the XYZ actuator 6 by applying a fraction of the voltage used to move the cantilever 1 vertically (Z) to that portion of the actuator 6 which moves the cantilever 1 in the X direction. Hoh et al., "Friction Effects on Force Measurements with an Atomic Force Microscope" Langmuir, 3 Aug., 1993. Typically, the part of the XYZ actuator 6 that controls the motion in the X direction (or Y direction) is significantly more sensitive (by a factor of about 15) to voltage than the part that controls motion in the Z or vertical direction. In other words, the X direction (or Y direction) actuator typically causes significantly larger motions than the Z direction actuator if the same voltage is applied to the actuator. In addition, the X-Y compensation is accomplished by moving the probe in the X direction by a small distance relative to the distance moved in the Z direction during the indenting process. Thus, only a small percentage of the voltage applied to the Z actuator needs to be applied to the X actuator, typically about 1%, corresponding to a motion of the probe at an angle of 12 degrees from vertical. An acceptable range of voltage applied to the X actuator is often between 0 to 6% of the voltage applied to the Z actuator, corresponding to angles ranging from 0 to 50 degrees measured from vertical. These percentages are typical for the preferred actuator, a piezoelectric tube. This compensation can also be done to both the X and Y scan axis to remove any asymmetry that the scanner may have in those directions, i.e., the Z motion may give some unwanted X and/or Y motion (FIGS. 10a–d).

In the preferred embodiment in which the XYZ actuator 6 comprises a piezo tube, the X-Y compensation is performed by calculation and application of a ratio of voltages applied to the X and Z components of the piezo tube such that the tip 2 moves a certain amount in X (horizontally) for each increment of Z (vertical) motion. In this manner, the tip 2 moves at an angle away from vertical that has been found to reduce the extraneous tip forces. The appropriate angle is not easily generalized due to asymmetries and hysteresis in the commonly used scanners. However, neglecting those problems, the necessary angle is ordinarily calculated by the following equation: tan q=X/Z, where q is the angle of declination described by the cantilever 1 at zero deflection, X is the distance to be added in the horizontal direction during indentation, and Z is the vertical distance moved by the scanner during indentation. Because q is known, it may thus be used to give the ratio of X motion to Z motion, and that ratio is then converted to a ratio of voltages to be applied to the piezo tube or XYZ actuator 6 during indenting.

The difficulty lies in compensation for motion that is not predicted by trigonometry alone. Thus, some amount of compensation may have to be determined experimentally, as discussed by Jan Hoh in "Friction Effects on Force Measurements with an Atomic Force Microscope", or by other methods such as optically measuring flex in the cantilever apart from simple deflection. For example, such optical measurement may be accomplished by periodic tracing of points along the long axis of the cantilever 1 with the laser 11 and displacement sensor 10 otherwise used for measuring only deflection of the cantilever 1.

Figure 13A:
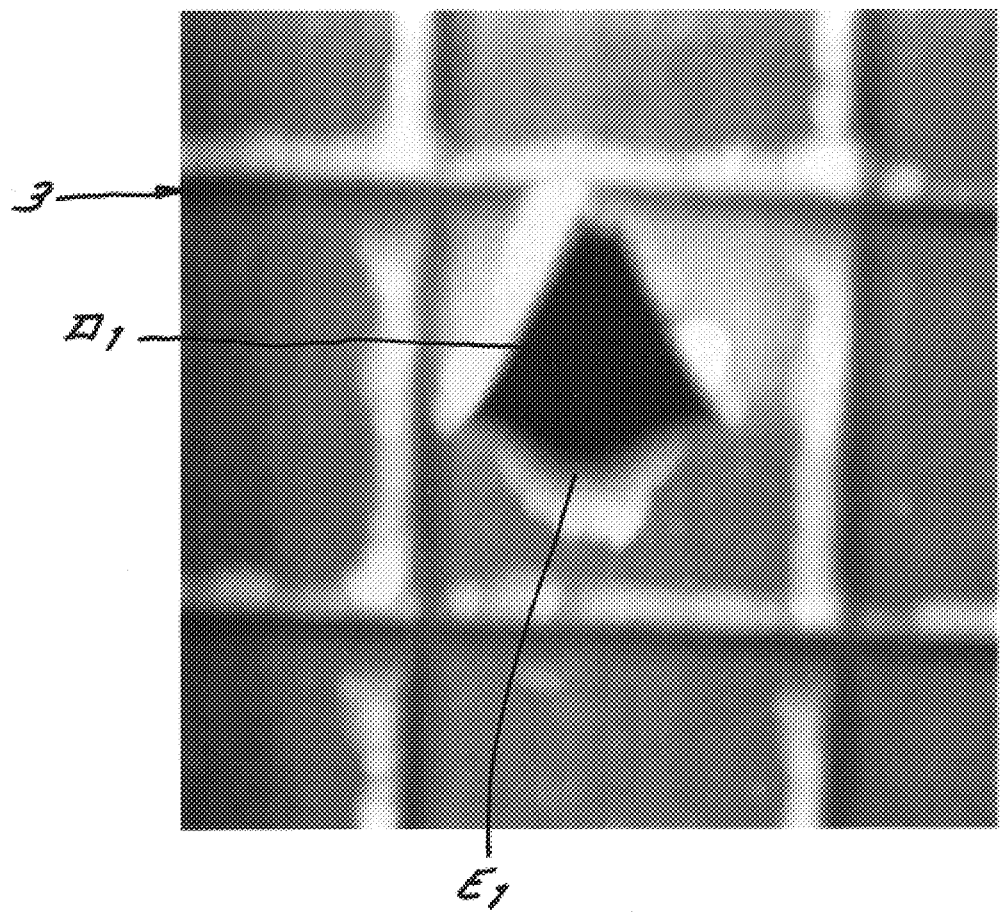
Figure 13B:
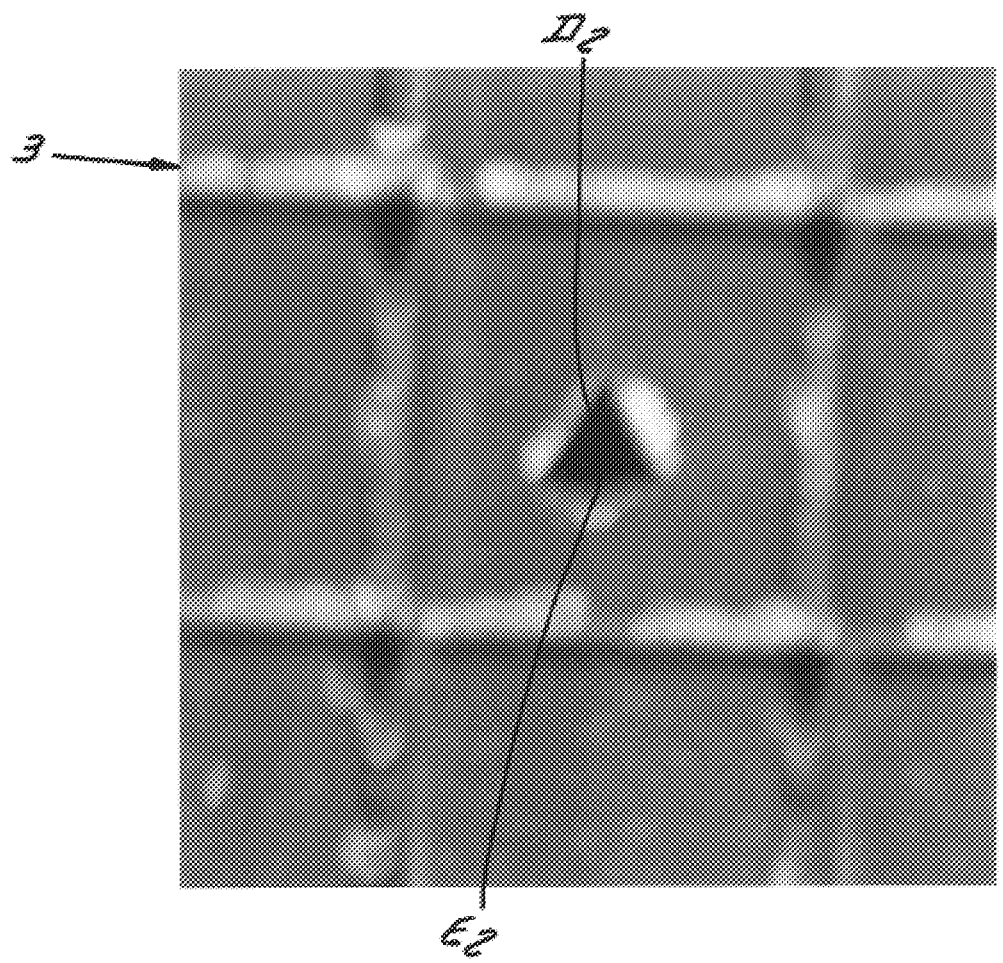
Figure 13C:
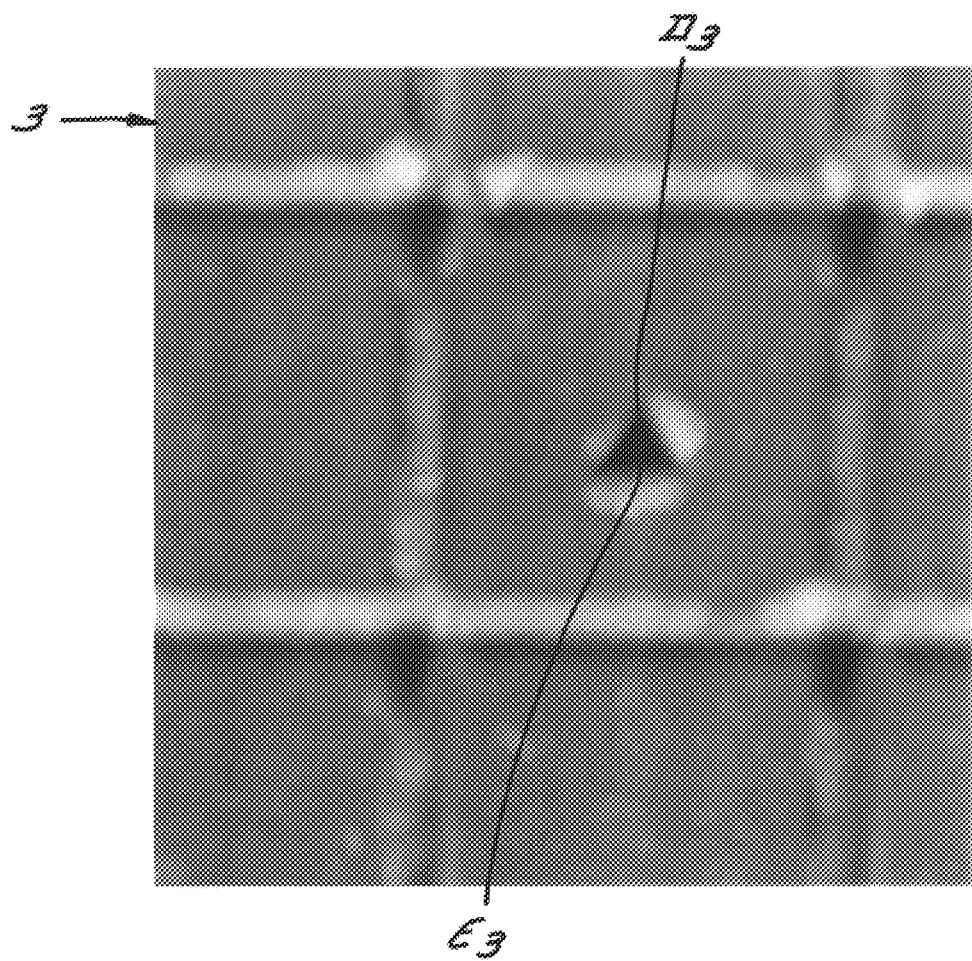

The beneficial effects of XY compensation are illustrated in FIGS. 13a–13e in which FIG. 13a illustrates a dent $D_1$ made during an indenting operation without X-Y compensation. The dent $D_1$ is relatively large because the measurement of the indentation force has been affected by the lateral force, and has a very jagged forward edge $E_1$ due to horizontal movement of the probe tip 2 relative to the sample surface during the indenting operation. FIG. 13b illustrates a dent $D_2$ which is formed during indenting of the same material and with the same "measured" force but with partial X-Y compensation. The dent $D_2$ is smaller than the dent $D_1$ because the actual force is less, and has a smoother forward edge $E_2$. Finally, FIG. 13c illustrates a dent $D_3$ formed by indenting the same material and with the same force but with more X-Y compensation. The dent $D_3$ is much smaller than the dent $D_1$ and has a much smoother front edge $E_3$. The correct X-Y compensation is sometimes determined by trial and error.

Figure 2:
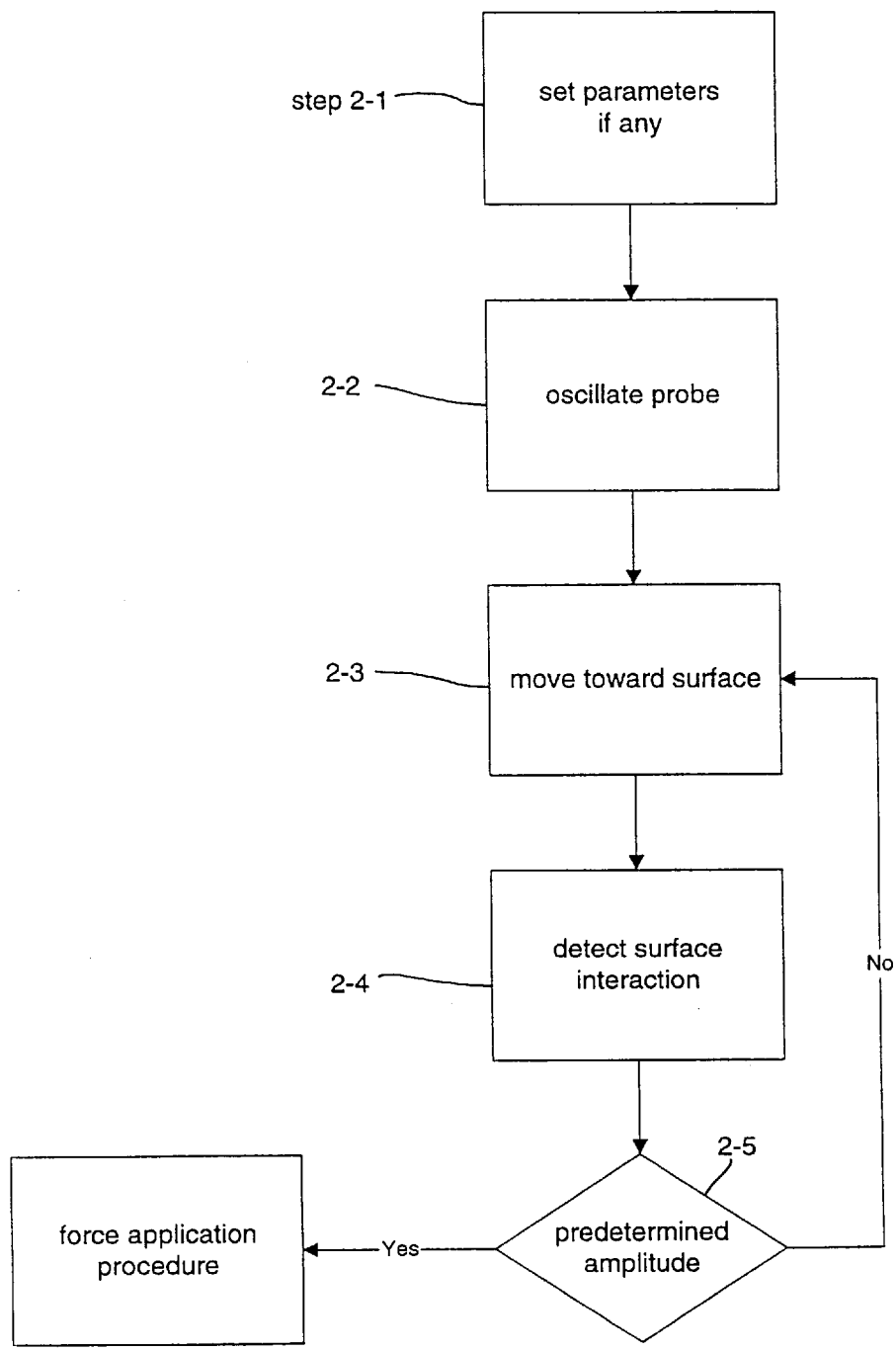
FIG. 2 is a flowchart of the approach phase of a method of operate atomic force microscope of the invention for creating a dent in a sample.
Figure 3:
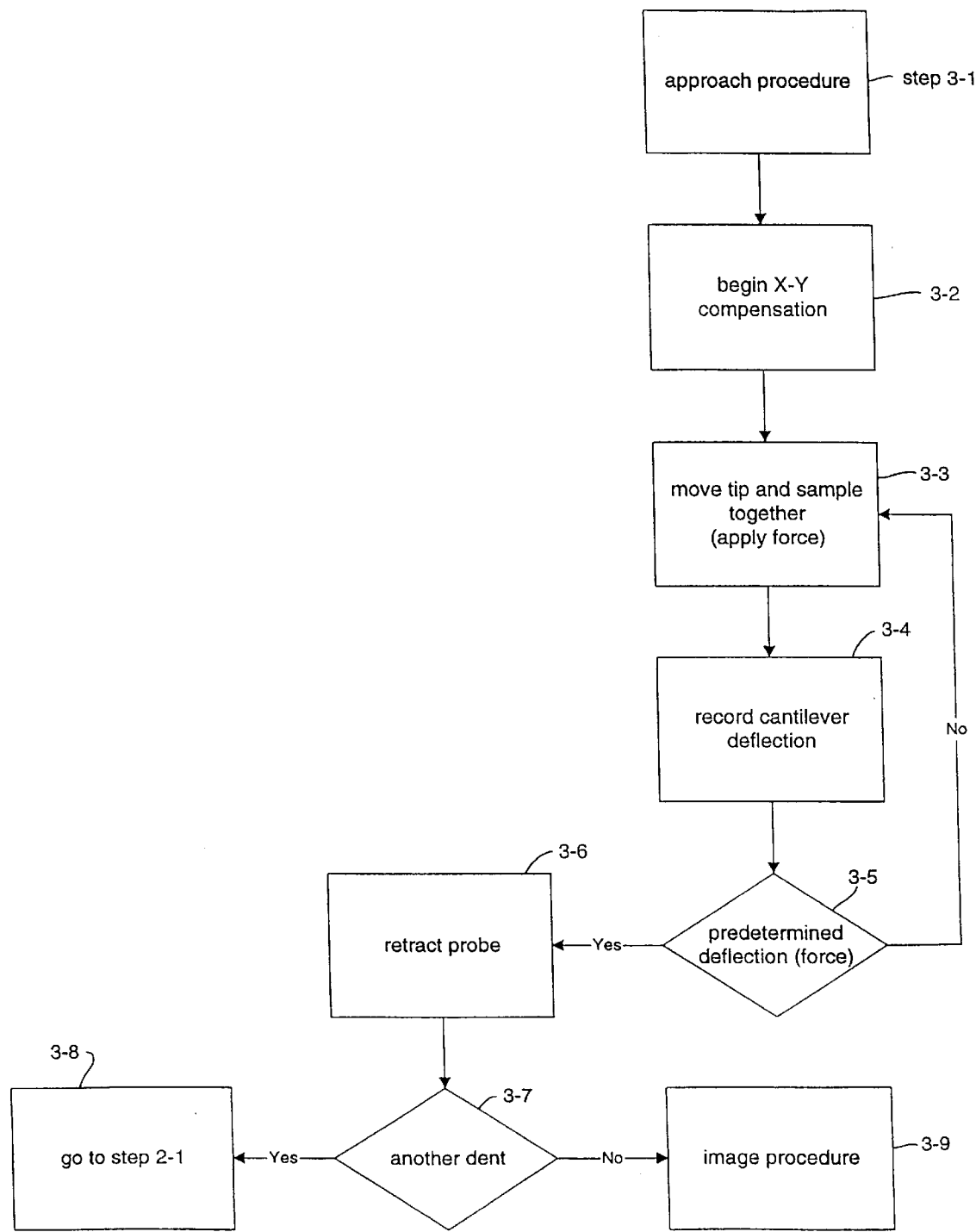
FIG. 3 is a flowchart of the force application phase of a method of operating the atomic force microscope of the invention to make a dent on a sample.

FIG. 2 is a flowchart representing the approach phase of a method of operating the preferred embodiment for making a dent on a sample. In step 21, the user sets any desired parameters for operation into the AFM control/computer 7 (often including, but not requiring or limited to, the predetermined deflection and amplitude for the indent and the amount of X-Y compensation). In step 2-2, the tip oscillator 5 begins oscillating the probe 9. In step 2-3, the XYZ actuator 6 moves the tip 2 toward the surface of the sample 3. When the oscillation amplitude of tip 2 is reduced by interaction between tip 2 and sample 3, such reduction (surface interaction) is detected by the laser 11 and the displacement sensor 10 (step 2-4). If the oscillation amplitude of the tip 2 has not been reduced to a predetermined amplitude (step 2-5), the system returns to step 2-3. If the oscillation amplitude of tip 2 does fall to the predetermined amplitude (step 2-5), the force application procedure begins (FIG. 3). Steps 2-3, 2-4 and 2-5 are usually done in a continuous manner until the setpoint is reached.

FIG. 3 is a flowchart representing the force application (indent) procedure phase of a method of operating the atomic force microscope of the invention. Upon completion of the approach procedure phase (step 3-1) (FIG. 2), the AFM control/computer 7 begins or continues X-Y compensation (step 3-2), to reduce undesirable horizontal forces between tip 2 and sample 3. In step 3-3, the tip 2 and sample 3 are forced against each other, preferably by operating XYZ actuator 6 to lower the tip 2 into indenting contact with the surface. While tip 2 and sample 3 are being forced together, the deflection of cantilever 1 is detected by laser 11 and displacement sensor 10 and recorded (step 3-4) in the AFM control/computer 7. If the cantilever deflection does not reach a predetermined deflection (force) (step 3-5), the system returns to step 3-3. If the cantilever 1 deflection does reach a predetermined deflection, thereby indicating that the indenting operation is complete (step 3-5), the probe 9 is retracted away from the surface of sample 3 (step 3-6). If, after the probe 9 is retracted in step 3-6, it is desired that more than one dent is to be made in the sample 3, the system returns to step 2-1 (step 3-8). If another dent is not desired, the system can then image the dent that has been made in intermittent contact mode (step 3-9).

Figure 11:
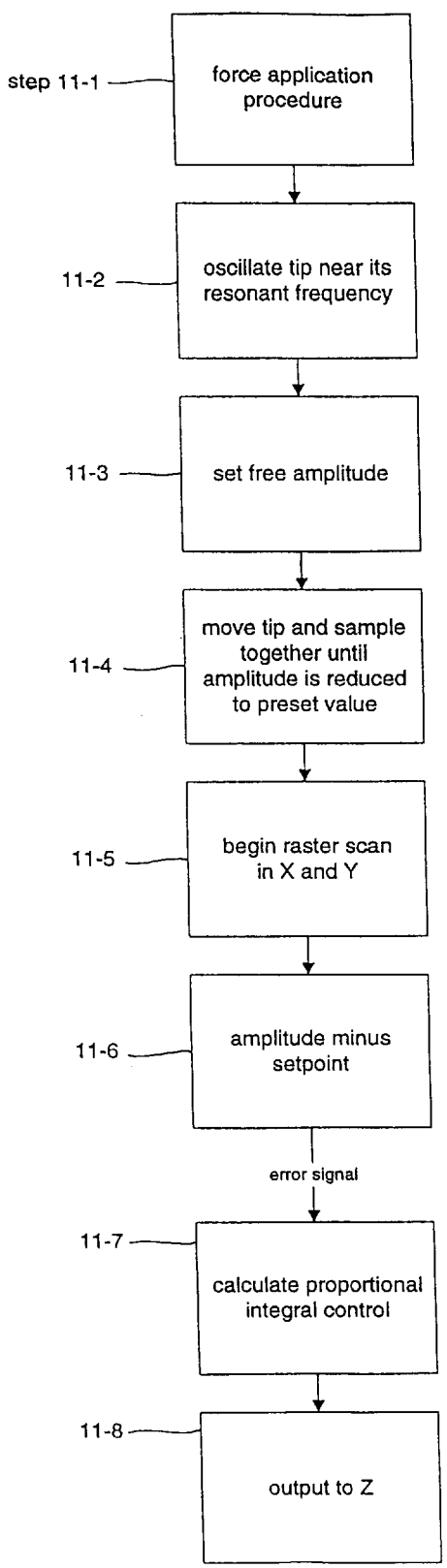
FIG. 11 is a flow chart representing the imaging and measurement phase of a method of operating the atomic force microscope of the invention.

FIG. 11 is a flowchart representing the imaging and measurement phase of a method of operating the atomic force microscope of the invention. After completion of the force application procedure (step 11-1), the tip 2 is oscillated at or near its fundamental resonant frequency or a higher resonance thereof (step 11-2). In step 11-3, the free oscillation amplitude of the tip 2 is determined and set by finding the tip 2's resonant frequency. In step 11-4, the tip 2 and the sample 3 are moved together, preferably by operation of the XYZ actuator 6, until the amplitude of the oscillations of tip 2 is reduced to a preset value (setpoint). The XYZ actuator 6 then begins scanning across the surface of a sample 3 in a raster pattern in the X-Y plane (step 11-5). Steps 11-4 and 11-5 could be in opposite order. In step 11-6, the oscillation amplitude error (amplitude−setpoint=error) is calculated (step 11-6) and fed back into a proportional and integral control calculation so that, if the amplitude of oscillation of the tip 2 is too large or too small, the cantilever 1 and sample 3 are moved together or apart, respectively, to maintain the oscillation amplitude essentially constant at the setpoint (step 11-7). See generally: U.S. Pat. No. RE34,331 by Elings et al.

Finally, the control is output to the Z portion of the XYZ actuator 6 piezo (step 11-8). While 'large' and 'small' are relative measures, the sensitivity of the correction is typically on the order of a few angstroms. The amplitude of oscillation of tip 2 as it taps on sample 3 is kept constant in this way, and the control signals are recorded in the AFM control/computer 7 as a function of the position of tip 2 in the X-Y plane. Alternatively, a separate Z sensor could be used to monitor the motion between the fixed end of the cantilever 1 and sample 3. The intermittent contact imaging process is described generally in U.S. Pat. No. 5,412,980 by Elings et al.

In this manner, the topography of the surface of the sample is recorded. The amplitude of oscillation of the probe 9 is usually greater than 20 nm to assure that the energy in the cantilever 1 is higher than that lost in each cycle by striking the sample surface, thereby preventing the probe tip from sticking to the sample surface. Data is obtained in the preferred embodiment based on the control signal produced to maintain the oscillation amplitude at a constant value equal to the setpoint, but it may also be recorded directly as a function of changes in the amplitude of oscillation of the probe 9 or from a separate Z sensor measuring the Z motion of the fixed end of the cantilever 1.

The surface can also be imaged before the indent in order to position the tip on a particular point on the surface, for instance, on a particular grain or other feature of a sample.

2. Scratching

Figure 14:
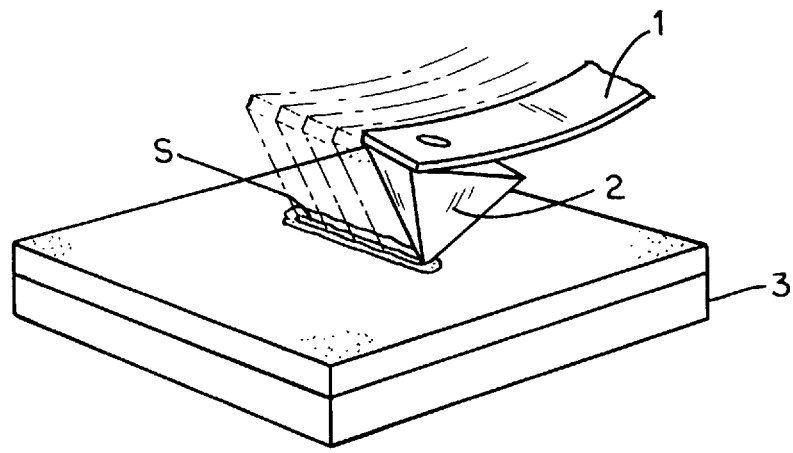
FIG. 14 is a schematic perspective view illustrating a scratching operation using an atomic force microscope constructed in accordance with the present invention.

Another embodiment of the invention is a method of producing scratches in the sample 3 rather than dents on the surface. With force applied, the probe tip 2 is moved across the surface of the sample 3 to form a scratch S in the sample surface as illustrated in FIG. 14. Scratching a sample is advantageous because it can provide data on hardness, film adhesion, toughness/durability and other characteristics of the surface. Such scratching can be done with preset distance, time, acceleration and force parameters, but such parameters are not required to be user determined. Like dents, the scratch or scratches are then imaged in intermittent contact mode with the same tip 2. The tip 2 may also be oscillated during scratching to provide useful force data.

Figure 4:
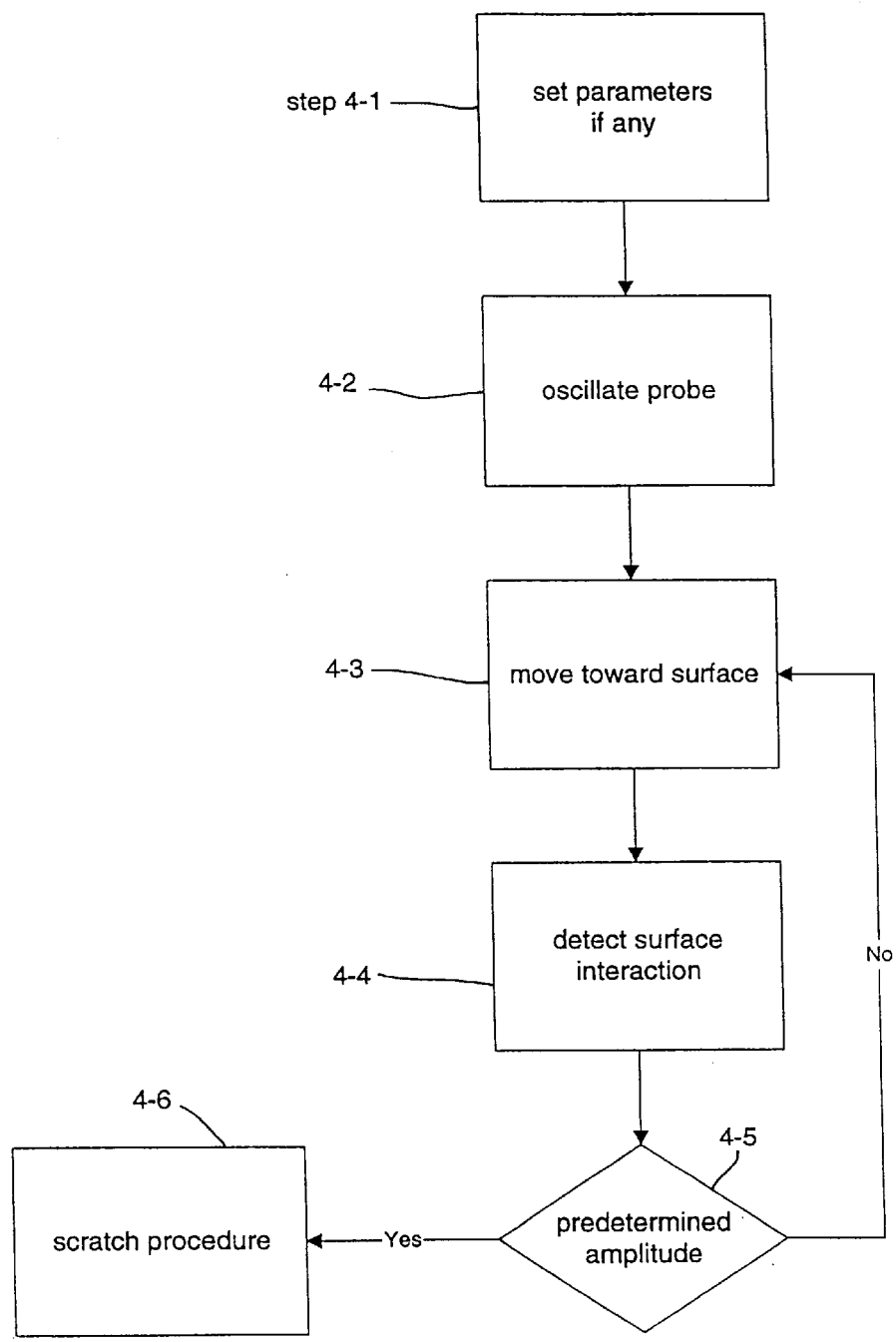
FIG. 4 is a flowchart of the approach phase of a method of operating the atomic force microscope of the invention for creating a scratch on a sample.

Scratches are created by a procedure similar to that for creating a dent with additional relative movement between the tip 2 and the sample 3. FIG. 4 is a flowchart representing the approach phase of a preferred method of producing a scratch or scratches. First, in step 4-1, the user sets any desired parameters for operation into an AFM control/computer 7 (often including but not requiring or limited to the predetermined deflection and amplitude for the indent, amount of X-Y compensation, scratch length, rate and angle, as measured in the horizontal plane, lateral deflection, force ramp values, and acceleration). In step 4-2, tip oscillator 5 begins oscillating probe 9. In step 4-3, XYZ actuator 6 moves the tip 2 toward the surface of sample 3, with or without X-Y compensation. When the oscillations of tip 2 are reduced by interaction between tip 2 and sample 3, such surface interaction is detected by laser 11 and displacement sensor 10 (step 4-4). If the oscillation amplitude of the tip 2 has not been reduced to a predetermined amplitude (step 4-5), the routine returns to step 4-3. If the oscillation amplitude of the tip 2 does fall to the predetermined amplitude (step 4-5), the force application and horizontal move (scratch) procedures begin (step 4-6) (FIG. 5).

Figure 5:
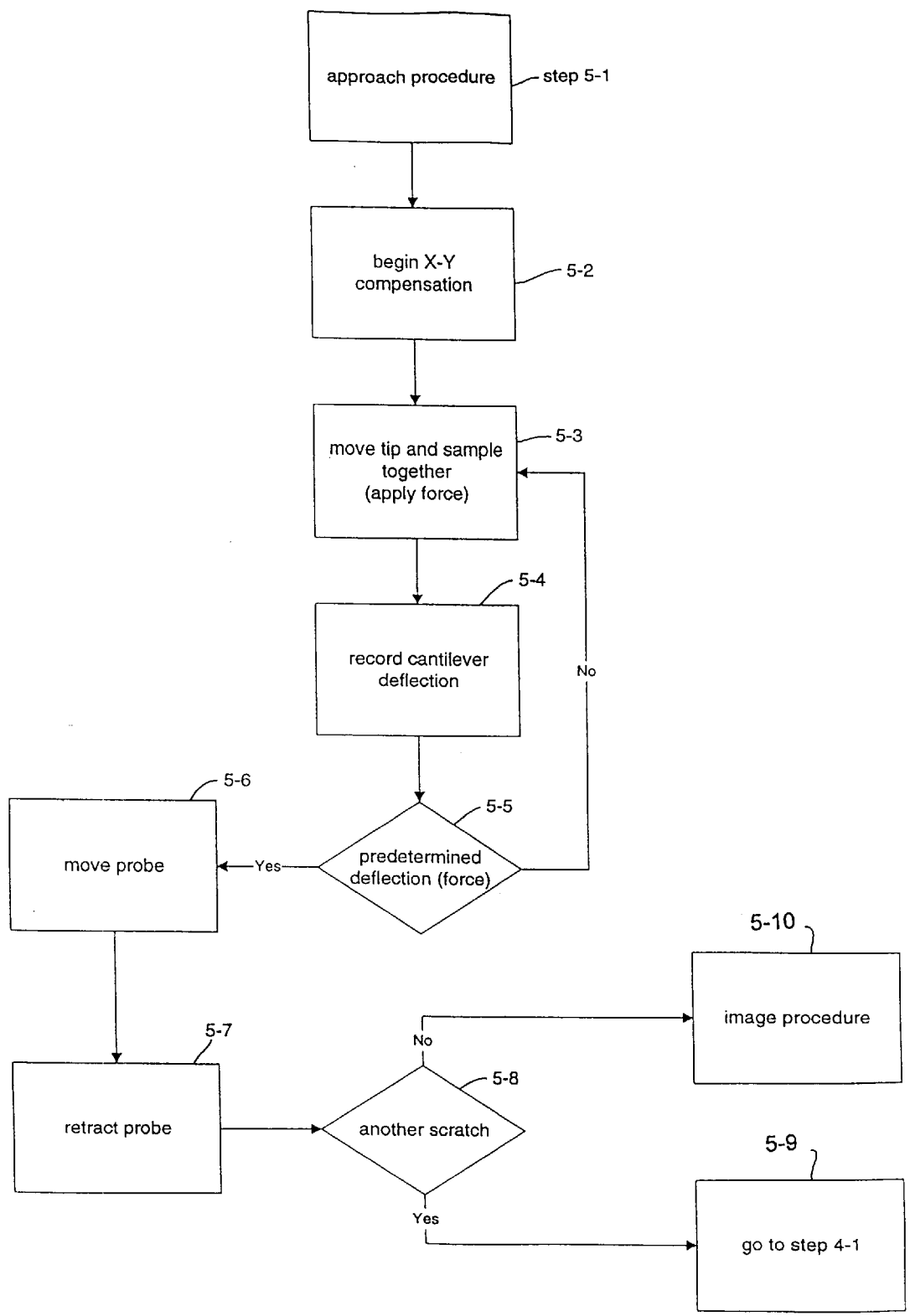
FIG. 5 is a flowchart of the force application and lateral drag phase of a method of operating the atomic force microscope of the invention to make a scratch on a sample.

FIG. 5 is a flowchart representing the force application and horizontal move (scratch) phase of a method of operating the atomic force microscope of the invention. Upon completion of the approach procedure phase (step 5-1) (FIG. 4), the AFM control/computer 7 begins or continues the X-Y compensation (step 5-2). In step 5-3, the tip 2 and sample 3 are forced against each other by action of the XYZ actuator 6. While tip 2 and sample 3 are being forced together, the deflection of cantilever 1 is detected by laser 11 and displacement sensor 10 and recorded (step 5-4) in the AFM control/computer 7. If the deflection of the cantilever 1 does not reach a predetermined deflection (force) (step 5-5), the system returns to step 5-3. If the cantilever 1 deflection does reach a predetermined deflection (force) (step 5-5), the probe 9 is moved laterally while in contact with the sample 3 (step 5-6). The probe 9 is then retracted (step 5-7). If, in step 5-8, it is desired that more than one scratch is to be made in the sample 3, the routine returns to step 4-1 (step 5-9) with an offset if it is desired to scratch in a different place and, optionally, at a different force. If another scratch is not desired, the system can then image the scratch that has been made (step 5-10) in intermittent contact mode.

Figure 8:
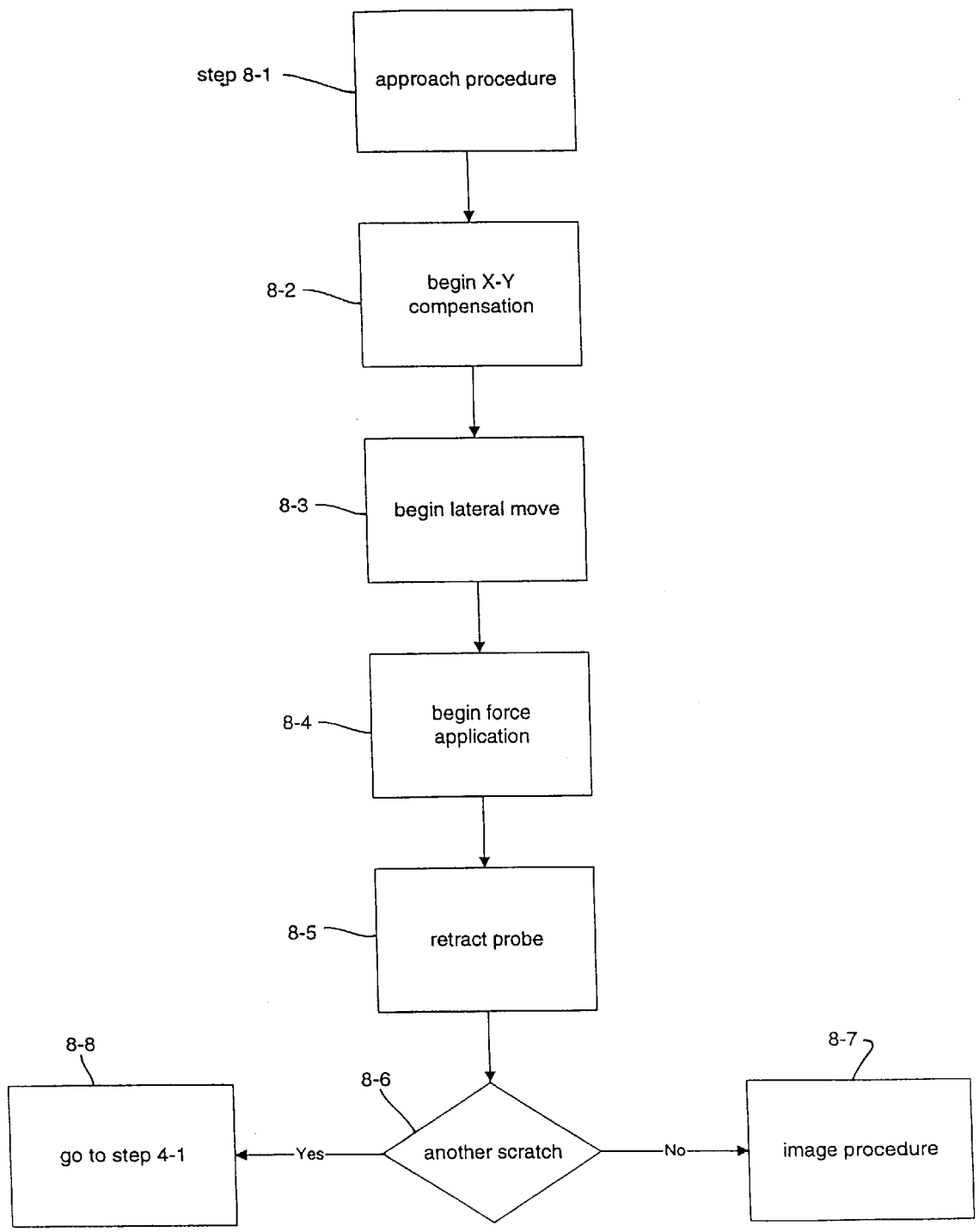
FIG. 8 is a flowchart of the force application and lateral drag phase of a method of operating the atomic force microscope of the invention to make a scratch on a sample with the force ramped.

While scratching, it is possible to ramp the force applied in the Z direction (vertically) so that the scratch varies in depth from an initial depth at the start to a final depth at the finish. Typically the depth of the scratch may be unknown while the scratch is being made, but may be subsequently measured. Thus, FIG. 8 is a flowchart representing the force application, lateral move, and force ramp procedure phase of a method of operating the atomic force microscope of the invention. Upon completion of the approach procedure phase (step 8-1) (FIG. 4), the AFM control/computer 7 begins X-Y compensation (step 8-2). In step 8-3, the XYZ actuator 6 is actuated to drive the probe 9 laterally while the tip 2 is in contact with the sample 3. In step 8-4, the tip 2 and sample 3 are forced against each other at the desired initial force value, and the probe 9 is driven horizontally with a ramped vertical force. Both the force ramp and the length of the scratch are preset. Thus, each continues until the scratching operation is complete. The probe 9 is then retracted (step 8-5). If, in step 8-6, it is desired that more than one scratch is made in the sample 3, the system returns to step 4-1 (step 8-8). If another scratch is not desired, the system can then image the scratch that has been made (step 8-7) in intermittent contact mode.

Figure 9:
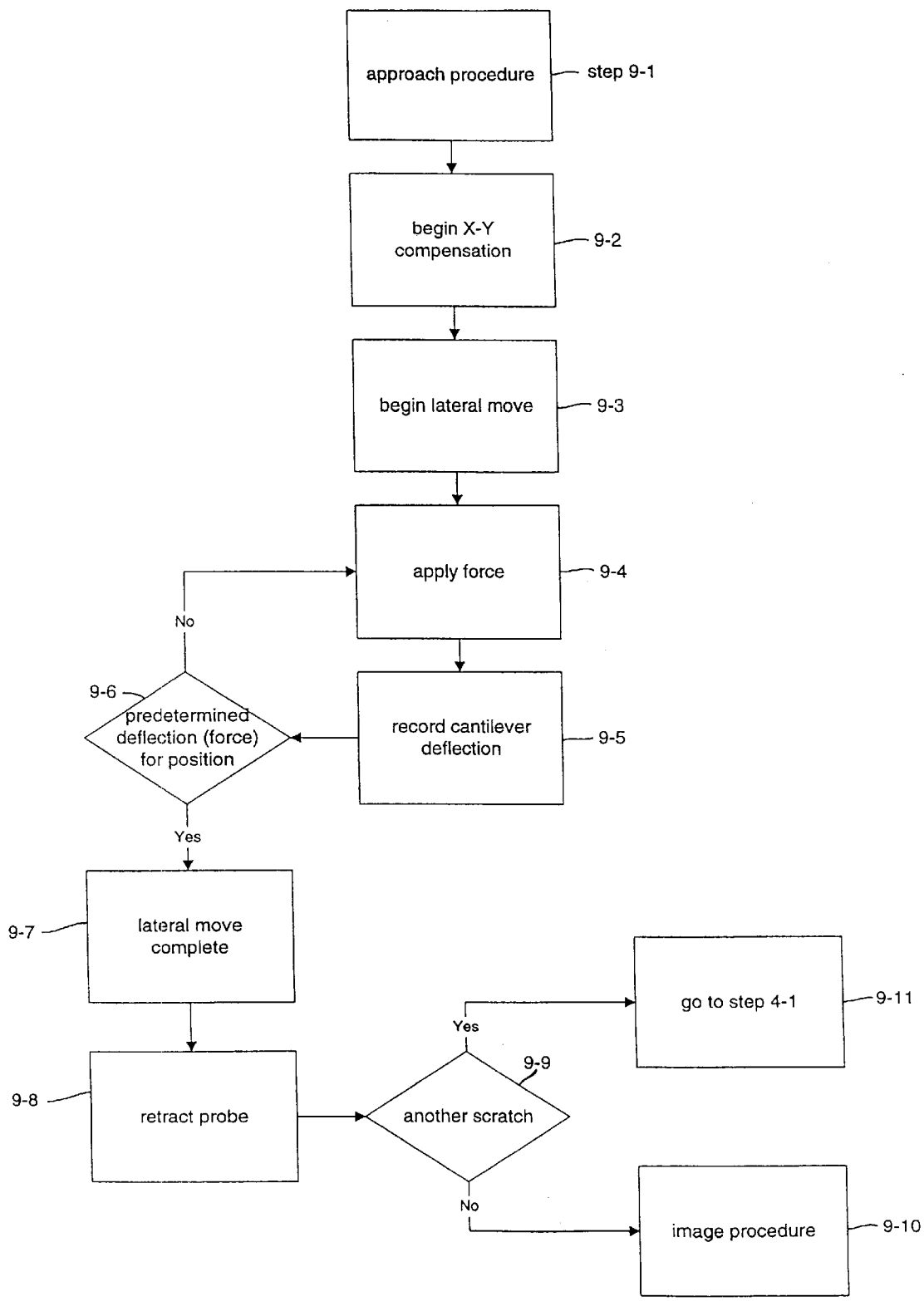
FIG. 9 is a flowchart of the force application and lateral drag phase of a method of operating the atomic force microscope of the invention to make a scratch on a sample with the force ramped and a feedback loop controlling the force as it is ramped.

The scratch procedure with a force ramp may also be controlled by a feedback loop to adjust the force applied during the scratching operation. Thus, FIG. 9 is a flowchart representing the force application, lateral move, and force ramp with feedback procedure phase of a method of operating the atomic force microscope of the invention. Upon completion of the approach procedure phase (step 9-1) (FIG. 4), the AFM control/computer 7 causes the XYZ actuator 6 to begin or continue X-Y compensation (step 9-2). In step 9-3, the probe 9 is driven laterally by the XYZ actuator 6 while in contact with the sample 3. In step 9-4, the tip 2 and sample 3 are forced against each other. While tip 2 and sample 3 are being forced together, the deflection of cantilever 1 is detected by laser 11 and displacement sensor 10 and recorded (step 9-5). If the cantilever 1 deflection does not reach a predetermined deflection (force) for the position of the probe in the lateral move (step 9-6), the routine returns to step 9-4 to increase the force. If the cantilever 1 deflection has reached the predetermined deflection for the position of the probe 9 in the lateral move (step 9-6), and the lateral move is complete (step 9-7), the probe 9 is then retracted away from the surface (step 9-8). If, in step 9-9, it is desired that more than one scratch is to be made in the sample 3, the routine returns to step 4-1 (step 9-11). If another scratch is not desired, the system can then image the scratch that has been made (step 9-10) in intermittent contact mode. Using this feedback, any force profile could be placed into the control. One could also use the lateral force sensor to measure or control the horizontal force during a scratch, or to detect an abrupt change, such as a thin film breaking loose from a substrate during scratching.

In either application of force ramping, it is to be understood that such a ramp may be set to increase, decrease, or vary the force applied during a particular scratch. In order to reduce or eliminate the effect of friction on the vertical force measurement, it may be desirable to move the cantilever at 90 degrees to the long axis of the cantilever or at an experimentally determined angle to the long axis as described in U.S. Pat. Nos. 5,400,647 and 5,553,487, which are hereby incorporated by reference.

3. Wear

Figure 15:
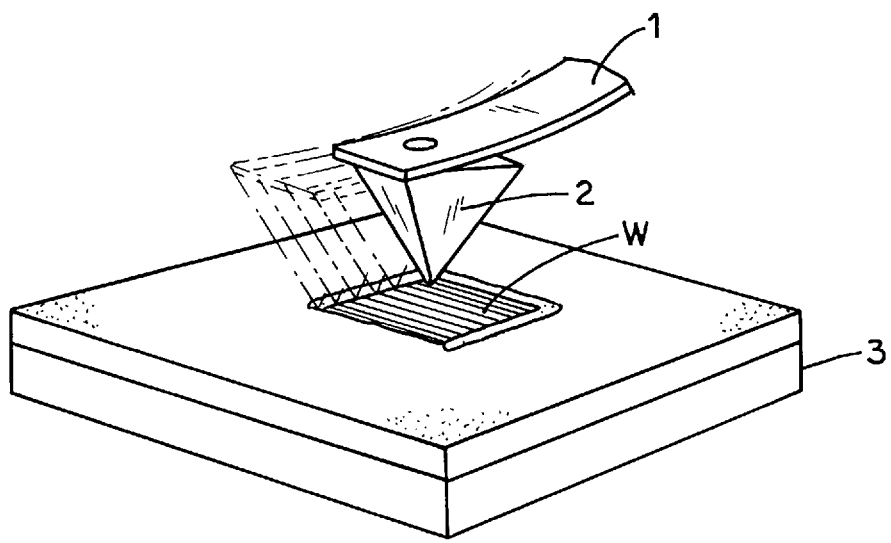
FIG. 15 is a schematic perspective view illustrating a wearing operation using an atomic force microscope constructed in accordance with the present invention.

Another embodiment of the invention is a method of producing wear on the sample 3 rather than dents or singular scratches. In this embodiment, the probe tip 2 is repeatedly moved across the surface of the sample 3 to wear a particular area W of the sample surface as illustrated in FIG. 15. Much like scratching, wearing a sample is advantageous because it can provide data on hardness, film adhesion, toughness/durability, film thickness and other characteristics of the surface. The user can preset the same parameters for scratches as well as others, such as area and scratches per area. Again, like individual dents and scratches, the wear is then imaged with the same tip in intermittent contact mode.

The thickness of a layer of a sample or a film on a substrate may be determined by wearing away the film or layer using the wear technique described above and measuring the vertical distance from the worn section to the unworn section. The thickness may sometimes be measured by breaking loose part of a film during scratching or wearing and then imaging the piece that has broken loose to determine its thickness.

Figure 6:
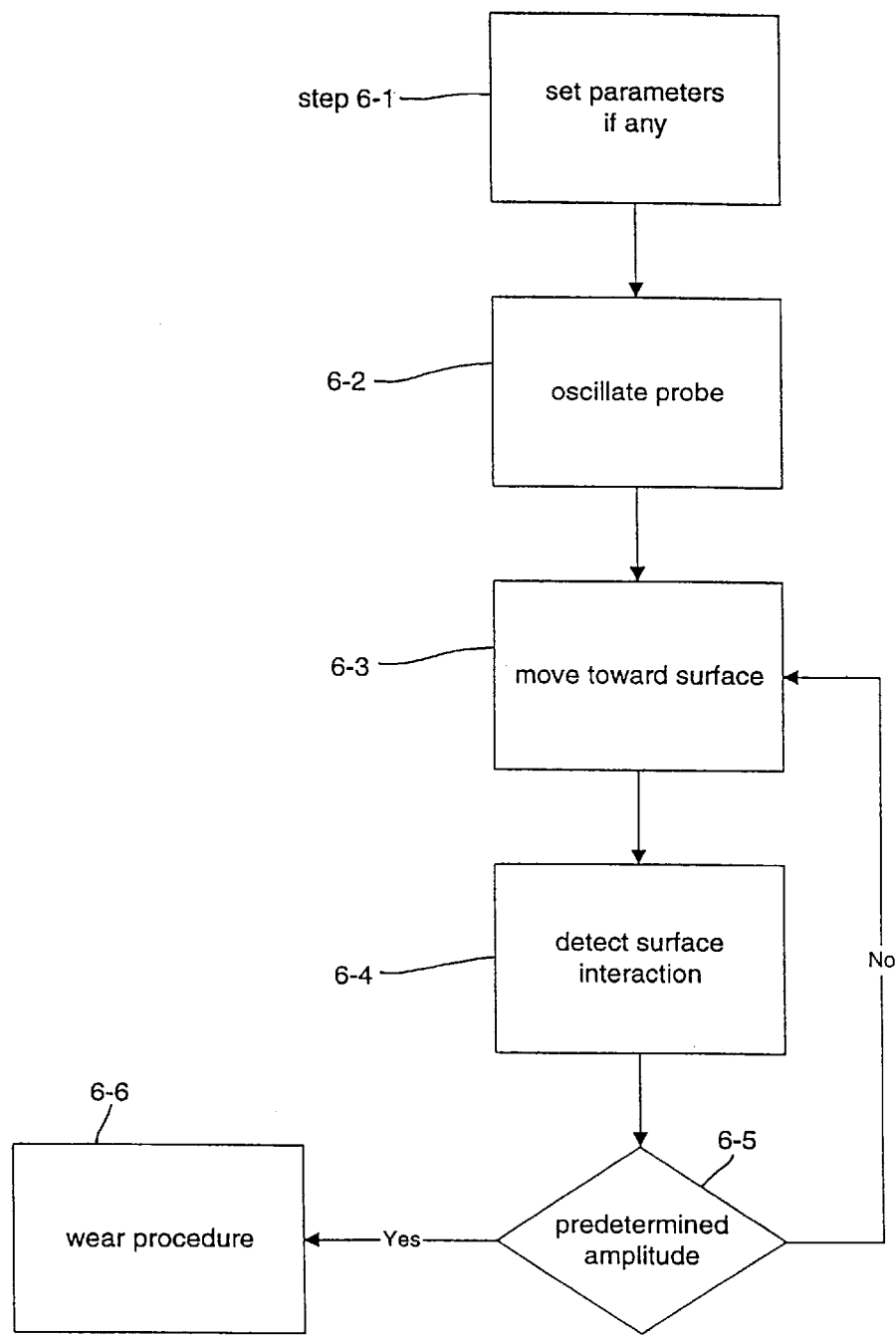
FIG. 6 is a flowchart of the approach phase of a method of operating the atomic force microscope of the invention for creating wear on a sample.
Figure 7:
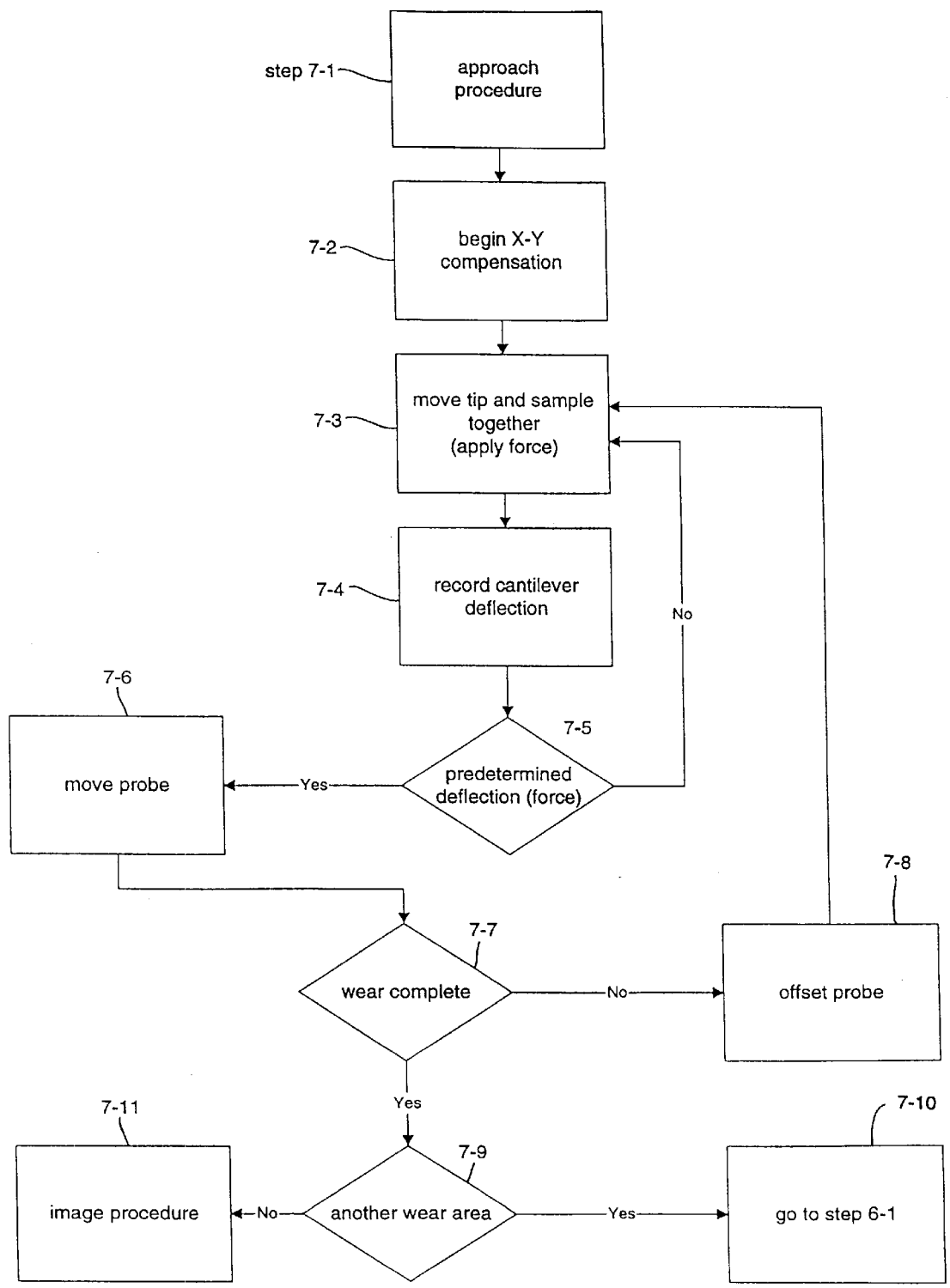
FIG. 7 is a flowchart of the force application and lateral drag phase of a method of operating the atomic force microscope of the invention to create wear on a sample.

Such wear is formed by a procedure similar to that for making a scratch, but it produces a broader area of wear and may use a blunter tip. FIG. 6 is a flowchart representing the approach procedure for wear testing of a sample and is substantially similar to that for scratching. FIG. 7 is a flowchart representing the force application and lateral moves (wear) procedure phase of a method of operating the atomic force microscope of the invention. Upon completion of the approach procedure phase (step 7-1) (FIG. 4), the AFM control/computer 7 begins X-Y compensation (step 7-2). In step 7-3, the tip 2 and sample 3 are forced against each other. While tip 2 and sample 3 are being forced together, the deflection of cantilever 1 is detected by laser 11 and displacement sensor 10 and recorded (step 7-4). If the cantilever deflection does not reach a predetermined deflection (step 7-5), the system returns to step 7-3. If the cantilever deflection does reach a predetermined deflection (step 7-5), the XYZ actuator then drives the probe 9 laterally while maintaining contact between the tip 2 and the sample 3 (step 7-6). This motion is along a single axis in the preferred embodiment, but it may include any two or three dimensional path the user desires. If the wear is not complete (step 7-7), the routine offsets the probe 9 to perform another scratch (step 7-8), and then returns to step 7-3. If the wear is complete (step 7-7), and the operator desires to wear another area (step 7-9), the routine goes to step 6-1 (step 7-10). If the wear is complete (step 7-7) and the operator does not desire to wear another area, or to wear the same area more (step 7-9), the routine goes to the imaging procedure (step 7-11).

Figure 7A:
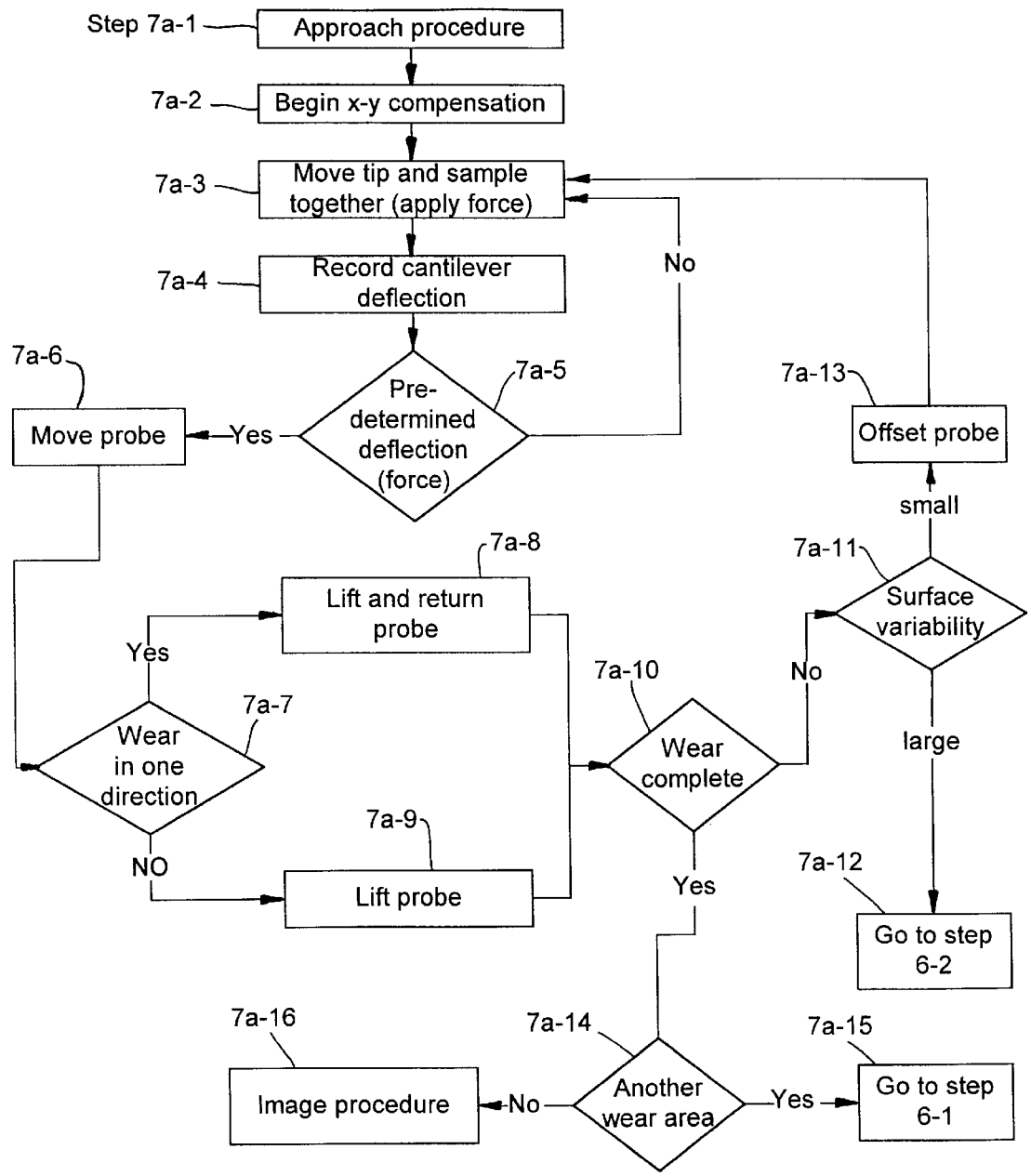
FIG. 7a is a flowchart of the force application and lateral drag phase of alternative methods of operating the atomic force microscope to create wear with additional steps comprising control of the direction of wear and adjustment for surface variability.

In the interest of simplicity, the description above does not describe whether the wear is performed with all scratches made in one direction, i.e., started at one side of the wear area, or in both directions, i.e., in a back and forth motion. FIG. 7a shows another embodiment where the probe 9 is lifted and returned to the starting side (step 7a-7) and then offset (step 7a-13) if the wear is to be in only one direction, or just lifted (step 7a-9) and offset (step 7a-13) to wear in both directions. Similarly, any pattern of scratching may be preset by the user to accomplish different types, rates, or methods of scratching. These different patterns, such as cross-hatching, knurling, parallel ruling, and even spirals are intended to be encompassed within this description.

Nor does the description above detail procedures for adjustment for the variability of the sample surface. This is necessary if the surface is so irregular that it makes the reference for zero force or deflection measured during the initial approach procedure inaccurate. Thus, FIG. 7a also shows another embodiment where the variability of the sample surface controls whether the approach procedure must be repeated (steps 7a- 11 and 7a-12) if the variability is large, or if the probe may simply be offset to create the next scratch (step 7a- 11).

Force ramping during wear is not described in detail here. However, it is to be understood that the scratching force ramp procedure, both with and without feedback, may be applied to wearing a sample to achieve a ramped wear in essentially the same manner as it is in scratching with the addition of the patterns available for wear. Also, the motion of the scanner may be at a particular angle with respect to the longitudinal axis of the cantilever 1.

In all of the above described embodiments, the XYZ actuator 6 is shown to move the fixed end of the cantilever 1 relative to the sample 3. It is to be appreciated that in place of the probe 9 being moved relative to the sample 3, the sample 3 may be moved relative to the tip 2 or probe 9 in any or all of the X, Y or Z directions by suitable movement of the chuck 4. Therefore, though the XYZ actuator 6 position control is shown in the preferred embodiment to control all three directions, the probe 9 could be maintained stationary and the sample 3 moved. For example, the sample 3 may be moved in the X and Y directions relative to the probe 9 while the probe 9 is moved in the Z direction relative to the sample 3. For simplicity of description, the various movements are as shown in the Figures, but, as indicated above, the invention is not limited to these specific structures.

Dents, scratches and wear on a sample may be combined in any order desired, but for simplicity those combinations are not described here. It is, however, to be appreciated that any combination of the above embodiments is intended to be covered by the above discussion and accompanying claims and figures.

Although the invention has been described with reference to particular embodiments, it is to be appreciated that various adaptations and modifications may be made and the invention is only to be limited by the appended claims.

We claim:

1. A method of forming an indentation in a surface of a sample and of subsequently imaging the indentation, said method comprising:

(A) providing an instrument having a probe, said probe including a cantilever and a probe tip supported on said cantilever; then (B) forcing said probe tip against the sample surface with sufficient force to form the indentation in the sample surface; and then (C) imaging the indentation by operating said instrument in an intermittent contact mode such that said probe tip oscillates to repeatedly contact the sample surface without dragging across the sample surface;

wherein said step of forcing said probe tip against the sample surface is performed without substantial relative horizontal movement between said probe and the sample and produces a dent in the sample surface: and wherein said step of forcing said probe tip against the sample surface comprises 1) forcing said probe tip progressively deeper into the sample surface while measuring the force between said probe tip and the sample, and then 2) effecting relative movement of said probe tip away from the sample surface when the measured force reaches a predetermined force value.

2. A method as defined in claim 1, wherein the force between said probe tip and the sample is measured by measuring cantilever deflection.

3. A method of forming an indentation in a surface of a sample and of subsequently imaging the indentation, said method comprising:

(A) providing an instrument having a probe, said probe including a cantilever and a probe tip supported on said cantilever; then (B) forcing said probe tip against the sample surface with sufficient force to form the indentation in the sample surface; then (C) imaging the indentation by operating said instrument in an intermittent contact mode such that said probe tip oscillates to repeatedly contact the sample surface without dragging across the sample surface;

wherein said step of forcing said probe tip against the sample surface is performed during substantial relative lateral movement between said probe and the sample and produces a scratch in the sample surface; and (D) ramping the force between said probe tip and the sample during said relative lateral movement to produce a scratch in the sample surface with a depth that varies progressively along the length of the scratch.

4. A method of forming an indentation in a surface of a sample and of subsequently imaging the indentation, said method comprising:

(A) providing an instrument having a probe, said probe including a cantilever and a probe tip supported on said cantilever; then (B) forcing said probe tip against the sample surface with sufficient force to form the indentation in the sample surface; then (C) imaging the indentation by operating said instrument in an intermittent contact mode such that said probe tip oscillates to repeatedly contact the sample surface without dragging across the sample surface; and (D) positioning said probe over the sample surface prior to the step of forcing said probe tip against the sample surface, said positioning step comprising
  (1) effecting relative vertical movement of said probe towards the sample surface while driving said probe to oscillate, and
  (2) terminating said relative vertical movement when intermittent contact between said probe tip and the sample surface reduces the oscillation amplitude of said probe tip to a predetermined amplitude; wherein said predetermined amplitude is less than a free air oscillation amplitude of said probe tip at or near the resonant frequency but greater than 0.25 times the free air oscillation amplitude of said probe tip at or near the resonant frequency.

5. A method as defined in claim 4, wherein said predetermined amplitude is between 0.8 and 0.9 times the free air resonant oscillation amplitude.

6. A method of forming an indentation in a surface of a sample and of subsequently imaging the indentation, said method comprising:

(A) providing an instrument having a probe, said probe including a cantilever and a probe tip supported on said cantilever; then (B) forcing said probe tip against the sample surface with sufficient force to form the indentation in the sample surface; and then (C) imaging the indentation by operating said instrument in an intermittent contact mode such that said probe tip oscillates to repeatedly contact the sample surface without dragging across the sample surface;

wherein said cantilever extends at an acute angle with respect to the sample surface, and wherein said step of forcing said probe tip against the sample surface is performed by effecting relative vertical movement between a base of said cantilever and the sample, and further comprising compensating for extraneous forces arising between said probe tip and the sample by effecting relative horizontal movement between said base of said cantilever and the sample during said relative vertical movement so that the force between said probe tip and the sample remains essentially normal to said cantilever.

7. A method as defined in claim 6, wherein the magnitude X of the relative horizontal movement during the compensating operation is a function of $(Z)(\tan(a))$, where:

"a" is the angle of declination described by said cantilever at zero cantilever deflection, and "Z" is the magnitude of the vertical movement of said probe tip during said step of forcing said probe against the sample surface.

8. A method of forming an indentation in a surface of a sample and of subsequently imaging the indentation, said method comprising:

(A) positioning a probe of an atomic force microscope over the sample surface, said probe including a cantilever and a probe tip mounted on a free end of said cantilever, said positioning step including
  (1) moving said probe vertically towards the sample surface while driving said probe to oscillate, and
  (2) terminating said vertical movement when intermittent contact between said probe tip and the sample surface reduces the oscillation amplitude of said probe tip to a predetermined setpoint;
then (B) forcing said probe tip against the sample surface with sufficient force to form the indentation in the sample surface, said forcing step including
  (1) forcing said probe tip progressively deeper into the sample surface while measuring the force between said probe tip and the sample, and
  (2) retracting said probe tip when the measured force reaches a designated threshold; and then (C) imaging the indentation by operating said atomic force microscope in an intermittent contact mode such that said probe tip oscillates to repeatedly contact the sample surface without dragging across the sample surface, said imaging step including
  (1) driving said probe to oscillate at or near a resonant frequency of said probe,
  (2) moving said probe vertically towards the sample surface,
  (3) terminating vertical movement of said probe towards the sample surface when intermittent contact between said probe tip and the sample surface reduces the oscillation amplitude of said probe tip to a preset value less than a free oscillation amplitude of said probe tip when it is not in contact with the sample surface, then
  (4) moving said probe horizontally while controlling the vertical distance between a base of said cantilever and the sample surface to maintain the probe tip oscillation amplitude essentially constant, thereby obtaining an indication of the topography of the sample surface.

9. A method as defined in claim 8, wherein said cantilever extends at an acute angle with respect to the sample surface, and wherein the step of forcing said probe tip against the sample surface is performed by movement of said base of said cantilever vertically towards the sample, and further comprising compensating for extraneous forces arising between said probe tip and the sample by moving said base of said cantilever horizontally during the vertical movement so that the force between said probe tip and the sample remains essentially normal to said cantilever.

* * * * *